US011382906B2

(12) United States Patent
Burback et al.

(10) Patent No.: US 11,382,906 B2
(45) Date of Patent: *Jul. 12, 2022

(54) COMPOSITIONS AND METHODS FOR REDUCING MUSCLE CONTRACTION

(71) Applicants: Battelle Memorial Institute, Columbus, OH (US); Jessica Catherine Bright, Dublin, OH (US)

(72) Inventors: Brian L. Burback, Hilliard, OH (US); Jessica Catherine Bright, Dublin, OH (US); Jerry D. Johnson, Dublin, OH (US)

(73) Assignees: Jessica Catherine Bright, Dublin, OH (US); Battelle Memorial Institute, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/695,306

(22) Filed: Nov. 26, 2019

(65) Prior Publication Data

US 2020/0171010 A1 Jun. 4, 2020

Related U.S. Application Data

(63) Continuation of application No. 15/885,987, filed on Feb. 1, 2018, now Pat. No. 10,702,510.

(60) Provisional application No. 62/453,582, filed on Feb. 2, 2017.

(51) Int. Cl.
| | |
|---|---|
| *A61K 31/4425* | (2006.01) |
| *A61P 41/00* | (2006.01) |
| *A61K 31/15* | (2006.01) |
| *A61P 21/02* | (2006.01) |
| *A61K 31/444* | (2006.01) |
| *A61K 9/00* | (2006.01) |
| *A61J 1/14* | (2006.01) |
| *A61K 45/06* | (2006.01) |
| *A61P 43/00* | (2006.01) |

(52) U.S. Cl.
CPC ............. *A61K 31/444* (2013.01); *A61J 1/14* (2013.01); *A61K 9/0019* (2013.01); *A61K 31/15* (2013.01); *A61K 31/4425* (2013.01); *A61K 45/06* (2013.01); *A61P 21/02* (2018.01); *A61P 41/00* (2018.01); *A61P 43/00* (2018.01); *A61J 2205/30* (2013.01)

(58) Field of Classification Search
CPC ..... A61K 31/15; A61K 31/4425; A61P 21/02; A61P 41/00
See application file for complete search history.

(56) References Cited

U.S. PATENT DOCUMENTS 10,702,510 B2 7/2020 Burback et al.

OTHER PUBLICATIONS

Sidell et al., "Intramuscular and intravenous administration of small doses of 2-pyridinium aldoxime methochloride to man," J. Pharm. Sci. 60(8):1224-28. PMID: 4945277. (Year: 1971).*
"Pralidoxime Chloride Injection (Auto-Injector), for use in nerve agent poisoning only" DailyMed—FDA, downloaded from https://dailymed.nlm.nih.gov/dailymed/fda/fdaDrugXs1.cfm?setid=a16ac225-bb32-4b27-bb66-9e152cf065eb&type=display, on Apr. 23, 2018, 7 pgs.
Berend, S., et al., "The antidotal efficacy of the bispyridinium oximes K027 and TMB-4 against tabun poisoning in mice," Chemico-Biological Interactions, 2010, 187:291-294, 4 pgs.
Burback, B.L., et al., "Special Edition Volume of MMB4 DMS," International Journal of Toxicology, 2013, 32(Suppl. 2):3S-4S, 2 pgs.
Clark, A.P.-Z., et al., "Good Manufacturing Practice: Manufacturing of a Nerve Agent Antidote Nanoparticle Suspension," International Journal of Toxicology, 2013, 32(Suppl. 2):5S-17S, 13 pgs.
Dixon, H., et al., "MMB4 DMS Nanoparticle Suspension Formulation with Enhanced Stability for the Treatment of Nerve Agent Intoxication," International Journal of Toxicology, 2013, 32(Suppl. 2):18S-29S, 12 pgs.
Dube, S.N., et al., "Effect of 2-pyridine aldoxime (2-PAM) on innervated & denervated rat diaphragm," Indian J Med Res, Mar. 1986, 83:314-317, 4 pgs.
Goyer, G.R., "Action of pyridine-2-aldoxime methochloride (PAM) on neuromuscular transmission in vitro and in vivo," Canadian Journal of Physiology and Pharmacology, 1968, 46:757-764, 8 pgs.
Hafeez, Khawaja Rashid, et al. "Postoperative complications with neuromuscular blocking drugs and/or reversal agents in obstructive sleep apnea patients: a systematic review." *BMC anesthesiology* 18.1 (2018): 91.
Harvilchuck, J.A., et al., "Efficacy and Pharmacokinetic/Pharmacodynamic Study of I,I'-Methylenebis{4-[(hydroxyamino)methyl]pyridinium} Dimethanesulfonate in Guinea Pigs and Rhesus Macaques Exposed to Cyclosarin," International Journal of Toxicology, 2013, 32(Suppl. 2):108S-117S, 10 pgs.
Harvilchuck, J.A., et al., "In Vivo Acetylcholinesterase Reactivation in Male Guinea Pigs and Rhesus Macaques Following Cyclosarin Exposure and Treatment with I,I'-Methylenebis{4-[(hydroxyamino)methyl] pyridinium} Dimethanesulfonate," International Journal of Toxicology, 2013, 32(Suppl. 2):99S-107S, 9 pgs.
Héritier, F., et al., "Sniff Nasal Inspiratory Pressure: A Noninvasive Assessment of Inspiratory Muscle Strength," Am J Respir Crit Care Med, 1994, 150:1678-1683, 6 pgs.
Hong, S.P., et al., "Comparative Toxicokinetics of MMB4 DMS in Rats, Rabbits, Dogs, and Monkeys Following Single and Repeated Intramuscular Administration," International Journal of Toxicology, 2013, 32(Suppl. 2):38S-48S, 11 pgs.

(Continued)

*Primary Examiner* — Theodore R. Howell
(74) *Attorney, Agent, or Firm* — Susanne A. Wilson; Frank Rosenberg

(57) ABSTRACT

Disclosed herein are methods of reducing muscle contraction in a diaphragm or peripheral muscle(s) of a patient sufficient to permit a surgical procedure. The methods may comprise the step of administering an oxime or pharmaceutically acceptable salt thereof to a subject in need thereof in an amount sufficient to achieve said reduced muscle contraction/neuromuscular blockade. Kits and articles of manufacture comprising a container having a label and a composition are also disclosed.

16 Claims, 22 Drawing Sheets

(56) References Cited

OTHER PUBLICATIONS

Hong, S.P., et al., "Evaluations of In Vitro Metabolism, Drug-Drug Interactions Mediated by Reversible and Time-Dependent Inhibition of CYPs, and Plasma Protein Binding of MMB4 DMS," International Journal of Toxicology, 2013, 32(Suppl. 2):75S-87S, 13 pgs.
Hong, S.P., et al., "Pharmacokinetics of MMB4 DMS in Rats, Rabbits, and Dogs Following a Single IV Administration," International Journal of Toxicology, 2013, 32(Suppl. 2):30S-37S, 8 pgs.
Johnson, J.D., et al., Eds., International Journal of Toxicology, Jul./Aug. 2013, 32(Suppl. 2), 4 pgs.
Laroche, C.M., et al., "Clinical Significance of Severe Isolated Diaphragm Weakness," The American Review of Respiratory Disease, Jan. 1988, 138(4):862-866, 5 pgs.
Lusiak, B.D., et al., "Absorption, Distribution, Metabolism, and Excretion of $^{14}$C-MMB4 DMS Administered Intramuscularly to Sprague-Dawley Rats and New Zealand White Rabbits," International Journal of Toxicology, 2013, 32(Suppl. 2):88S-98S, 11 pgs.
Musílek, Kamil, K. Kuca, and Daniel Jun. "Evaluation of potency of known oximes (pralidoxime, trimedoxime, HI-6, methoxime, obidoxime) to in vitro reactivate acetylcholinesterase inhibited by pesticides (chlorpyrifos and methylchlorpyrifos) and nerve agent (Russian VX)." Acta Medica-Hradec Kralove—50.3 (2007): 203.
Osheroff, M.R., et al., "Comparative Toxicology Studies in Sprague-Dawley Rats, Rhesus Monkeys, and New Zealand White Rabbits to Determine a Non Observed Adverse Effect Level for I,I'-Methylenebis[4-(hydroxyamino)methyl]-pyridinium] Dimethanesulfonate," International Journal of Toxicology, 2013, 32(Suppl. 2):59S-74S, 16 pgs.
Peter, John V., John L. Moran, and Petra Graham. "Oxime therapy and outcomes in human organophosphate poisoning: an evaluation using meta-analytic techniques." Critical care medicine 34.2 (2006): 502-510.
Reddy, V.K., et al., "Effectiveness of Oximes 2-PAM and HI-6 in Recovery of Muscle Function Depressed by Organophosphate Agents in the Rat Hemidiaphragm: An In Vitro Study," Fundamental and Applied Toxicology, 1991, 17:746-760, 15 pgs.
Roche, B.M., et al., "MMB4 DMS: Cardiovascular and Pulmonary Effects on Dogs and Neurobehavioral Effects on Rats," International Journal of Toxicology, 2013, 32(Suppl. 2):49S-58S, 10 pgs.
Worek, F., et al., "The value of novel oximes for treatment of poisoning by organophosphorus compounds," Pharmacology & Therapeutics, 2013, 139:249-259, 11 pgs.
Worek, F., et al., "Treatment of tabun poisoned guinea-pigs with atropine, HLö7 or HI 6: effect on respiratory and circulatory function," Archives of Toxicology, 1994, 68:231-239.
International Search Report and Written Opinion dated May 22, 2018 for Application No. PCT/US2018/016355, 14 pgs.
Representative Anesthetic Agents Used for Animal Experiments and Analgesics; 2016, pp. 104 to 122, http://www.clar.med.toboku.ac.jp/dara/kitei/12rh/hoi7; accessed on Jan. 7, 2021.
1st Office Action from Japanese Application No. 2019542438 dated Aug. 31, 2021.
Translation of 1st Office Action from Japanese Application No. 2019542438 dated Aug. 31, 2021.
Snider, Thomas H. et al. J. Toxicol. Sci., (2016) 41, 511-521, "Toxicity and median effective doses of oxime therapies against percutaneous organophosphorous pesticide and nerve agent challenges in the Hartley guinea pig."

* cited by examiner

COMPOSITIONS AND METHODS FOR REDUCING MUSCLE CONTRACTION

CROSS-REFERENCE TO RELATED APPLICATIONS

This application claims priority to and benefit of U.S. Ser. No. 15/885,987, filed Feb. 1, 2018, published as U.S. Pub. No. 2018/0214433 on Aug. 2, 2018, which claims priority to and benefit of U.S. Ser. No. 62/453,582, filed Feb. 2, 2017, the contents of which are incorporated by reference in its entirety and for all purposes.

GOVERNMENT RIGHTS

This invention was funded by Contract Number CBR-NIAC SP0700-00-D-3180, Delivery Order (DO) 0798 and Technical Area Task (TAT) 0756 and Contract Number GS00Q14ADU402 with a DO Number of W911QY-16-F-0074. The government has certain rights in this invention.

BACKGROUND OF THE INVENTION

Neuromuscular blocking drugs are essential to the current discipline of surgery. More specifically, these drugs are used for routine procedures as endotracheal intubation, mechanical ventilation and muscular relaxation/paralysis. Naguib and Lien (Miller's Anesthesia), reporting on the history and clinical use of muscular relaxants (includes the drugs classified as neuromuscular blockers), wrote "the use of neuromuscular blockers in the operating room is quite common and has been important in the growth and development of anesthesia and surgery." Such muscle relaxing agents not only "revolutionized the practice of anesthesia but also started the modern era of surgery and made possible the explosive development of cardiothoracic, neurologic and organ transplant surgery."

Muscle relaxation is generally produced by depolarizing or non-depolarizing neuromuscular blockade. Depolarizing neuromuscular blockade, (e.g. using succinylcholine) causes failure of action potential generation, thereby leading to blockade. In contrast, non-depolarizing neuromuscular blockade, (e.g. using agents such as pancuronium, vecuronium, atracurium, mivacurium, rocuronium, pipecuronium, doxacurium, cisatracurium, rapacuronium) occurs due to a competitive inhibition of the acetylcholine receptor.

Despite the routine nature of surgical procedures, currently available neuromuscular blockers are insufficient in many aspects. In particular, it would be advantageous to have a drug that would specifically target a muscle type, e.g. diaphragm vs skeletal muscle, that would have rapid onset (e.g. seconds), a short duration of action (e.g. minutes), an effect that could be repeated without diminution or tolerance for the duration of interest, a rapid recovery (e.g. seconds or minutes), with no residual effect on muscle function (e.g. complete return to normal neuromuscular function), and eliminated unchanged as the parent molecule, thereby precluding any activity of metabolites.

Current agents are lacking in one or more of these respects. Succinylcholine, for example, has a rapid onset and extremely short duration of action but cannot be repeatedly used due to rapid tolerance to its effects. Likewise, the current non-depolarizing neuromuscular blockers have their own types of limitations, which include duration of effect (e.g. short acting—mivacurium; intermediate acting—vecuronium, rocuronium, atracurium, cisatracurium; long acting—pancuronium, pipecuronium, d-tubocurarine, metocurine, doxacurium). Thus, there exists a need for improvement in the art, in particular, a therapeutic that meets one or more of the advantages listed above that is not provided by currently available agents.

The instant disclosure addresses one or more of the aforementioned needs in the art.

BRIEF SUMMARY

Disclosed herein are methods of reducing muscle contraction in a diaphragm of a patient sufficient to permit a surgical procedure. The methods may comprise the step of administering an oxime or pharmaceutically acceptable salt thereof to a subject in need thereof in an amount sufficient to achieve said reduced muscle contraction. Kits and articles of manufacture comprising a container having a label and a composition are also disclosed.

DETAILED DESCRIPTION OF THE INVENTION

Definitions

Figure 1:
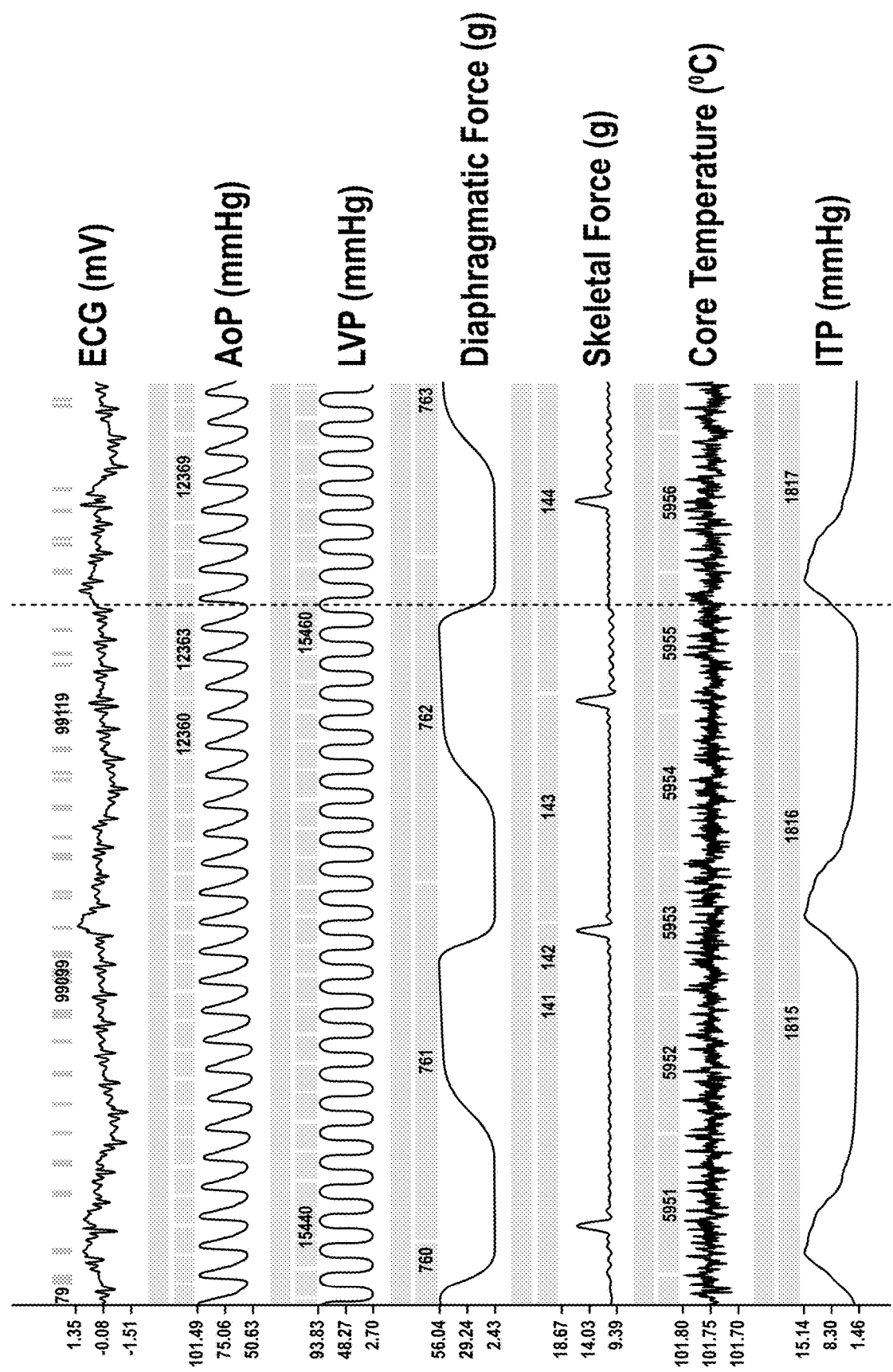
FIG. 1 depicts representative tracings (10 seconds) at baseline in an anesthetized rabbit preparation, showing (top to bottom) the ECG, arterial pressure (AoP), left-ventricular pressure (LVP), intrinsic diaphragmatic contraction, stimulated skeletal muscle contractions, core body temperature, and intra-tracheal pressure (ITP) signals.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some aspects, the terms refer to humans. In further aspects, the terms refer to children.

"Therapeutically effective amount" relates to the amount or dose of an active compound or composition described herein that will lead to one or more therapeutic effect, in particular, one or more desired beneficial effects. A therapeutically effective amount of a substance can vary according to factors such as the disease state, age, sex, and weight of the subject, and the ability of the substance to elicit a desired response in the subject. Dosage regime may be adjusted to provide the optimum therapeutic response. For example, several divided doses may be administered daily or the dose may be proportionally reduced as indicated by the exigencies of the therapeutic situation.

The phrase "pharmaceutically acceptable," as used in connection with compositions of the disclosure, refers to molecular entities and other ingredients of such compositions that are physiologically tolerable and do not typically produce untoward reactions when administered to a subject (e.g., human). In certain aspects, as used herein, the term "pharmaceutically acceptable" means approved by a regulatory agency of a Federal or a state government or listed in the U.S. Pharmacopeia or other generally recognized pharmacopeia for use in mammals (e.g., humans).

The term "carrier" applied to pharmaceutical compositions of the disclosure refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are described in "Remington's Pharmaceutical Sciences" by E. W. Martin, 18th Edition.

The term "compound," as used herein, is also intended to include any salts, solvates, or hydrates thereof. All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The terms "pharmaceutically acceptable salts" or "a pharmaceutically acceptable salt thereof" refer to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as The Merck Index. Any suitable constituent can be selected to make a salt of an active drug discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives can also be suitable for use in the compositions and methods disclosed herein. A salt of a compound of this disclosure may be formed between an acid and a basic group of the compound, such as an amino functional group, or a base and an acidic group of the compound, such as a carboxyl functional group. According to another aspect, the compound is a pharmaceutically acceptable acid addition salt. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one aspect, pharmaceutically acceptable acid addition salts include those formed with mineral acids such as hydrochloric acid and hydrobromic acid, and especially those formed with organic acids such as maleic acid.

As used herein, the term "oxime" is intended to mean a chemical compound belonging to the imines, with the general formula $R^1R^2C=N\ O\ H$, where $R^1$ is an organic side-chain and $R^2$ may be hydrogen, forming an aldoxime, or another organic group, forming a ketoxime. O-substituted oximes form a closely related family of compounds. Amidoximes are oximes of amides with general structure RC=NOH. Examples of such are provided in the "Handbook of Toxicology of Chemical Warfare Agents," edited by Ramesh C. Gupta, copyright 2009, ISBN 978-0-12-374484-5. In general, the oximes contemplated for the described use include both the mono- and bis-quaternary ring structures, in particular, having a nitrogen-containing ring wherein at least one nitrogen is ammonium (i.e., a positive charged ring(s)/nitrogen(s)), and which can be characterized as having a cationic center, and which block the nicotinic receptor at a neuromuscular junction such as that found in the diaphragm, skeletal muscle, or the like.

1,1'-Methylenebis{4-[(hydroyimino) methyl]-pyridinium}dimethanesulfonate (MMB4 DMS) is a member of the bisquaternary pyridium aldoximes group and has been studied for the treatment of organophosphorus (OP) nerve agent exposure. Burback et al, International Journal of Toxicology, 32 (Supplement 2) 3S-4S 2013. MMB4 was first synthesized in 1959, and the dimehanesulfonate (DMS) salt of MMB4 is being evaluated as a replacement for currently fielded 2-PAM as a treatment for OP nerve agent-induced toxicity.

MMB4 and other molecules classified as oximes have, up until Applicant's discovery and to the best of Applicant's knowledge, not been evaluated for neuromuscular blockade/muscle relaxation. Rather, such agents have been widely used in the treatment of acetylcholinesterase (AChE) inhibition because they have the capacity to bind with very lethal inhibitors (e.g. nerve agents, insecticides), thereby allowing AChE to become reactivated.

Although AChE reactivation has been the primary reason for developing MMB4 and other oximes as therapeutic agents, recent mechanistic studies have indicated that MMB4 and other oximes (i.e. 2-PAM) also have non-depolarizing neuromuscular blockade activity. Applicant has found that MMB4 and/or other oximes may be used as drugs to purposefully cause neuromuscular blockade to assist appropriate medical practices and operating procedures. This class of chemicals is believed to have characteristics, e.g. rapid onset, optimal duration, specificity to the diaphragm, etc. that may improve upon the current choices of neuromuscular blockers. Without intending to be limited by theory, MMB4 and other oximes are believed to have as their pharmacological action the binding of nicotinic receptors at the neuromuscular junction, thereby precluding the effect of acetylcholine, the neurotransmitter, the initiator of skeletal muscle contractions.

Specifically, without intending to be limited by theory, it is believed that MMB4 and/or other oximes bind to the nicotinic receptors at the neuromuscular junctions and block the neurotransmitter acetylcholine (ACh) from initiating a muscle contraction. This type of blockade enhances working conditions needed by surgeons and medical teams during abdominal and thoracic operations that require cessation of skeletal muscle contractions, especially of the diaphragm. Such use could be used as a supplement to or replacement of currently used neuromuscular blockers. The compounds identified by Applicant can be used in medical practices and operating procedures to elicit paralysis of the diaphragm and peripheral skeletal muscles, thereby facilitating the surgeon and medical team performing abdominal and/or thoracic operations and procedures. Not only do the disclosed compounds appear to have pharmacological action like that of currently used neuromuscular blockers (i.e. rocuronium, vecuronium, cisatracurium) but the disclosed compounds are more efficacious toward causing diaphragm muscle cessation relative to the peripheral skeletal muscles or vice versa; an opposite of and a more favorable pharmacological action than the currently used neuromuscular blockers.

The properties of the novel use of the disclosed oxime compounds are particularly unexpected in view of the structures of the oximes as compared to agents currently used as neuromuscular blockers. The oximes, including, for example, MMB4, have completely different structures from currently used neuromuscular blockers. Table 1 shows the name and chemical structure for currently used neuromuscular blockers and oximes such as MMB4, 2-PAM, and HI-6.

TABLE 1

Chemical structure for currently used neuromuscular blockers versus oximes such as MMB4, 2-PAM, and HI-6

| Name | Chemical Structure |
|---|---|
| Currently Used Non-Depolarizing Neuromuscular Blockers | |
| Cisatracurium (Besilate salt) | 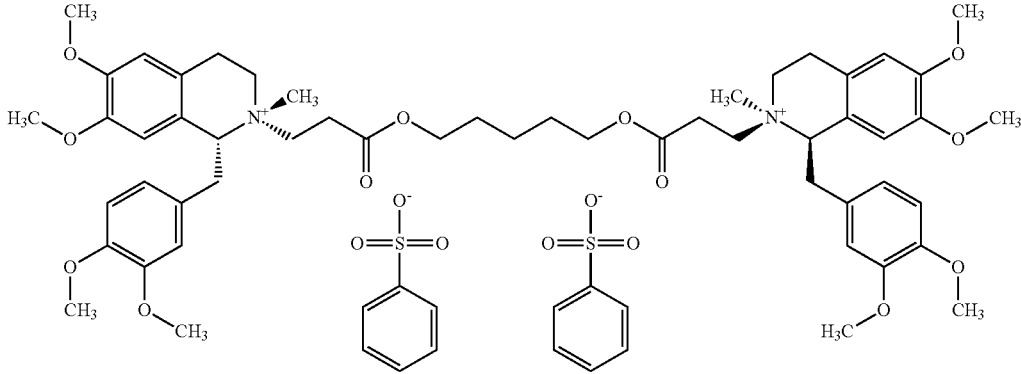 |
| Rocuronium | 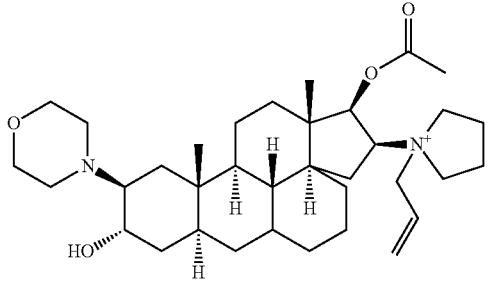 |

TABLE 1-continued

Chemical structure for currently used neuromuscular blockers versus oximes such as MMB4, 2-PAM, and HI-6

| Name | Chemical Structure |
| --- | --- |
| Vecuronium (Bromide salt) | (structure shown) |

Novel Neuromuscular Blockers (Oximes)

| | |
| --- | --- |
| MMB4 and other oximes, e.g. 2-PAM, and HI-6 | HI-6 (structure shown)<br>MMB4 (structure shown)<br>2-PAM (structure shown) |

In one aspect, a method of reducing muscle contraction in a diaphragm of a patient sufficient to permit a surgical procedure is disclosed. In this aspect, the method may comprise the step of administering an oxime or pharmaceutically acceptable salt thereof to a subject in need thereof in an amount sufficient to achieve said reduced neuromuscular blockade or muscle contraction. The oxime may be, in some aspects, selected from one or more of the following:

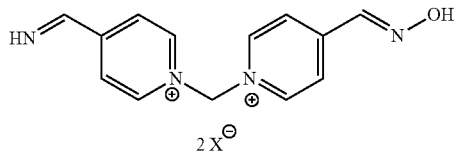 [SMILES: N=Cc1cc[n+](C[n+]2ccc(/C=N/O)cc2)cc1]

(methoxime or "MMB4");

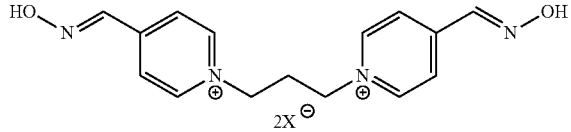 [SMILES: O/N=C/c1cc[n+](CCC[n+]2ccc(/C=N/O)cc2)cc1]

(trimedoxime or "TMB-4" or 1,3-bis(5-hydroxyiminomethylpyridinium)-propane bromide));

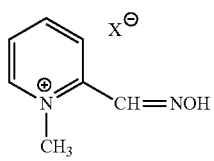

(pralidoxime or "2-PAM" or 2-hydroxyiminomethyl-1-methylpyridinium chloride);

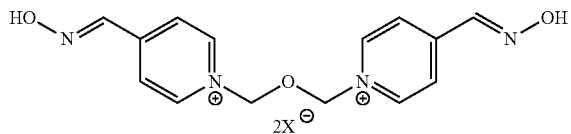 [SMILES: O/N=C/c1cc[n+](COC[n+]2ccc(/C=N/O)cc2)cc1]

(obidoxime or [1,3-bis(4-hydroxyimino-methylpyridinium)-2-oxapropane);

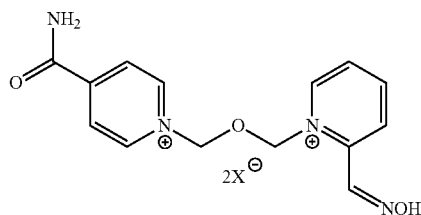

("HI-6" or [1-(2-hydroxyiminomethylpyridinium)-3-(4-carbamoylpryidinium)-2-oxapropane chloride],

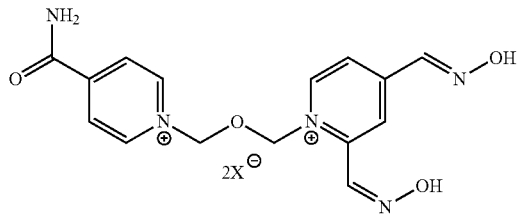 [SMILES: NC(=O)c1cc[n+](COC[n+]2ccc(/C=N/O)cc2/C=N\O)cc1]

("HLo-7" or (1-[2,4-bis(hydroxyiminomethylpyridinium)]-3-(4-carbamoylpyridinium)-2-oxapropane chloride);

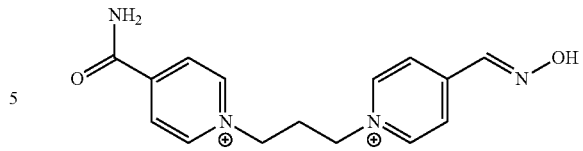

("K027" or [1-(4-hydroxyiminomethylpyridinium)-3(4-carbamoylpyridinium)-propane bromide];

and pharmaceutically acceptable salts thereof.

In one aspect, the oxime is MMB4 or a pharmaceutically acceptable salt thereof. In one aspect, the pharmaceutically acceptable salt may be selected from dichloride or dimethane sulfonate.

In one aspect, the oxime may be co-administered with an agent selected from a neuromuscular blocker, an amnestic agent, an analgesic agent, an anti-salivation agent, and a combination thereof. For example, the use of MMB4 or another oxime candidate as a neuromuscular blocker, e.g. during surgery, may require that it be combined with agents that produce amnesia (amnestic agents), analgesia (analgesic agents) and agents that reduce salivation. Amnestic agents commonly used in combination with a neuromuscular blocker include Propofol (administered IV) and isoflurane, sevoflurane or desflurane (administered by inhalation). Another class of amnestic agents commonly used are the benzodiazepines, e.g. midazolam, diazepam, etc., due to the retrograde amnestic properties. Analgesics that are commonly used include fentanyl and its derivatives, e.g. sufentanil, etc.; ketamine; nonsteroidal anti-inflammatory drugs (NSAID), e.g. toradol, etc.; Tylenol; local anesthetics, e.g. lidocaine, bupivacaine, ropivacaine, etc.; and morphine and its derivatives, e.g. hydromorphone. These analgesics are typically administered intravenously. Anti-salivation is commonly controlled by concomitant administration (IV) with glycopyrrolate.

In one aspect, a medicament for inducing neuromuscular blockade in an individual in need thereof is disclosed. The medicament, or composition, may comprise an oxime or pharmaceutically acceptable salt thereof.

The oxime may be any of the aforementioned oximes, in particular, MMB4 or a pharmaceutically acceptable salt thereof. The medicament may further comprise an agent selected from a neuromuscular blocker, an amnestic agent, an analgesic agent, an anti-salivation agent, and a combination thereof, and may be suited for administration via a route selected from intravenously, parenterally, intramuscularly, or a combination thereof. The oxime may be present in the composition at a concentration of from about 25 to about 500 mg/mL, or from about 50 to about 250 mg/mL or about 100 mg/mL oxime in a pharmaceutically acceptable carrier.

In one aspect, the oxime, or pharmaceutically acceptable salt thereof, may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of a composition suitable for administration to an individual. In certain aspects, the oxime or pharmaceutically acceptable salt thereof may be present in a composition comprising from about 25 to about 500 mg/mL, or from about 50 to about 250 mg/mL or about 100 mg/mL oxime or pharmaceutically acceptable salt thereof in a pharmaceutically acceptable carrier.

Dosage

As will be apparent to those skilled in the art, the ordinary skilled clinician or treating physician will readily appreciate determination of an appropriate dosage and regimen, and modification thereof.

Dosage from administration by these routes may be continuous or intermittent, depending, for example, upon the patient's physiological condition, whether the purpose of the administration is therapeutic or prophylactic, and other factors known to and assessable by a skilled practitioner.

In certain aspects, the dosage of the composition provided herein, based on weight of the active compound, administered to a subject may be at least about 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another aspect, the dosage of the composition comprising an oxime administered to a subject in need thereof is a unit dose of about 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The compositions may be administered in dosage forms such as intravenous (bolus or infusion), intraperitoneal, subcutaneous, or intramuscular forms all utilizing dosage forms well known to those of ordinary skill in the pharmaceutical arts.

A dosage regimen will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount can be readily determined by an ordinarily skilled physician The composition may be administered to a subject continuously or periodically.

The compositions may comprise suitable pharmaceutical diluents, excipients, vehicles, or carriers selected based on the intended form of administration, and consistent with conventional pharmaceutical practices. The carriers, vehicles etc. may be adapted to provide an additive, synergistically effective or therapeutically effective amount of the active compounds. Suitable pharmaceutical diluents, excipients, vehicles, and carriers are described in the standard text, Remington: The Science and Practice of Pharmacy (21st Edition. 2005, University of the Sciences in Philadelphia (Editor), Mack Publishing Company), and in The United States Pharmacopeia: The National Formulary (USP 24 NF 19) published in 1999.

In one aspect, a composition comprising the oxime may have pH from about 2 to 10, or about 2 to 3.

The disclosed compounds may be formulated for parenteral administration (e.g., formulated for injection via intravenous, intraarterial, subcutaneous, rectal, subcutaneous, intramuscular, intraorbital, intracapsular, intraspinal, intraperitoneal, or intrasternal routes). The compositions for parenteral administration may comprise an effective amount of the compound in a pharmaceutically acceptable carrier. Dosage forms may include solutions, suspensions, dispersions, emulsions or any other dosage form. Techniques and compositions for making dosage forms are known in the art. Typically, formulations for administration are sterile or are sterilized before administration.

In one aspect, the disclosed compositions can be used in various compositions adapted to induce neuromuscular blockade in patients as needed in surgical anesthesia. In various aspects, a compound of the invention produces, upon administration of an effective amount of the compound to a patient, a neuromuscular blockade.

In one aspect, a disclosed compound, administered by injection as a suitable solution, may produce neuromuscular blockade of sufficient completeness to enable the compound to effectively be used as an adjunct to anesthesia in major surgery. In various aspects, an effective amount of an inventive compound for administration to a human patient may be about 0.01-10 mg per kg patient bodyweight, or 0.1-1 mg per kg patient bodyweight. The compound can be administered in a manner known to the anesthesiologist or surgeon of ordinary skill in the art, using the methods and apparatus well known for this procedure in surgery.

In one aspect, the disclosure provides a composition comprising a compound of the invention and a pharmaceutically acceptable excipient. The composition can be adapted for parenteral administration to a human patient, comprising an injectable solution of the compound in a suitable biocompatible solvent. In various aspects, an injectable solution of a compound of the invention in a suitable solvent comprises about 1 mg/mL to about 10 mg/mL, or about 1 mg/mL to about 10 mg/mL, or about 2 mg/mL to about 9 mg/mL, or about 3 mg/mL to about 8 mg/mL, about 4 mg/mL to about 7 mg/mL, about 5 mg/mL to about 6 mg/mL of the compound per dose of the injectable solution. The solution can be administered via syringe, via intravenous drip, or via any of the techniques well known to the practitioner of the art.

Suitable carriers used in formulating liquid dosage forms for oral or parenteral administration may include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents may include alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)30-60 sorbitol poly(oleate)2-

4, poly(oxyethylene)15-20 monooleate, poly(oxyethylene) 15-20 mono 12-hydroxystearate, and poly(oxyethylene)15-20 mono-ricinoleate, polyoxyethylene sorbitan esters (such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del.), polyvinylpyrrolidone, alkyleneoxy modified fatty acid esters (such as polyoxyl 40 hydrogenated castor oil, cyclodextrins or modified cyclodextrins (e.g., beta-hydroxypropyl-cyclodextrin)), saccharide fatty acid esters (i.e., the condensation product of a monosaccharide (e.g., pentoses, such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a C4-C22 fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzine; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

In one aspect, a suitable biocompatible solvent may comprise sterile, pyrogen-free water. The solvent can further comprise isotonic NaCl, or other tonicity adjustment substances. In various aspects, the suitable biocompatible solvent can comprise alcohol, a polyethylene glycol, DMSO, or any mixture thereof, which can be neat or can be in a mixture with water. In various aspects, the dosage form can be adapted for frozen storage, such as by packaging in containers that can withstand freezing, bearing freeze-resistant labeling, and the like.

Other pharmaceutically acceptable solvents for use with the disclosed compounds are well known to those of ordinary skill in the art.

Exemplary solvents may include cyclodextrins or modified cyclodextrins (e.g., beta-hydroxypropyl-cyclodextrin) as well as oils rich in triglycerides, for example, safflower oil, soybean oil or mixtures thereof, and alkyleneoxy modified fatty acid esters such as polyoxyl 40 hydrogenated castor oil. Commercially available triglycerides include Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®.

Additional components may be included in the compositions of the disclosure for a variety of purposes well known in the pharmaceutical industry. These components will for the most part impart properties which enhance retention of the compound at the site of administration or conversely, facilitate the distribution of the active throughout the body, protect the stability of the composition, control the pH, facilitate processing of the compound into pharmaceutical formulations, and the like. Each of these components may be individually present in less than about 15 wt % of the total composition, or less than about 5 wt %, or, in other aspects, less than about 0.5 wt % of the total composition. Some components, such as fillers or diluents, may constitute up to 90 wt % of the total composition. Such additives include cryoprotective agents for preventing reprecipitation, surface active, wetting or emulsifying agents (e.g., lecithin, polysorbate-80, Tween® 80, Pluronic 60, polyoxyethylene stearate), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

In one aspect, a solid form pharmaceutical composition is provided (e.g. tablets, capsules, powdered, or pulverized form) comprising an oxime or pharmaceutically acceptable salt thereof.

After pharmaceutical compositions have been prepared, they can be placed in an appropriate container and labeled for treatment of an indicated condition. For administration of a composition, such labeling would include amount, frequency, and method of administration.

Kits

In one aspect, a kit is disclosed. The kit may comprise a composition comprising an oxime or pharmaceutically acceptable salt thereof and a pharmaceutically acceptable carrier; and a means for delivery of said composition to a human. In one aspect, the oxime may be one or more of the aforementioned oximes or pharmaceutically acceptable salt thereof. In one aspect, the oxime may be MMB4. The composition of the kit may be formulated for intravenous administration to an individual for surgical purposes.

The kit may be a package that houses a container which may contain a composition comprising an oxime or pharmaceutically acceptable salt thereof as disclosed herein, and also houses instructions for administering the agent or composition to a subject. In one aspect, a pharmaceutical pack or kit is provided comprising one or more containers filled with one or more composition as disclosed herein. Associated with such container(s) can be various written materials such as instructions for use, or a notice in the form prescribed by a governmental agency regulating the manufacture, use or sale of pharmaceuticals or biological products, which notice reflects approval by the agency of manufacture, use, or sale for human administration.

As there may be advantages to mixing a component of a composition described herein and a pharmaceutically acceptable carrier, excipient or vehicle near the time of use, kits in which components of the compositions are packaged separately are disclosed. For example, the kit can contain an active ingredient in a powdered or other dry form in, for example, a sterile vial or ampule and, in a separate container within the kit, a carrier, excipient, or vehicle, or a component of a carrier, excipient, or vehicle (in liquid or dry form). In one aspect, the kit can contain a component in a dry form, typically as a powder, often in a lyophilized form in, for example, a sterile vial or ampule and, in a separate container within the kit, a carrier, excipient, or vehicle, or a component of a carrier, excipient, or vehicle. Alternatively, the kit may contain a component in the form of a concentrated solution that is diluted prior to administration. Any of the components described herein, any of the carriers, excipients or vehicles described herein, and any combination of components and carriers, excipients or vehicles can be included in a kit.

Optionally, a kit may also contain instructions for preparation or use (e.g., written instructions printed on the outer container or on a leaflet placed therein) and one or more devices to aid the preparation of the solution and/or its administration to a patient (e.g., one or a plurality of syringes, needles, filters, tape, tubing (e.g., tubing to facilitate intravenous administration) alcohol swabs and/or the Band-Aid® applicator). Compositions which are more concentrated than those administered to a subject can be prepared. Accordingly, such compositions can be included in the kits with, optionally, suitable materials (e.g., water, saline, or other physiologically acceptable solutions) for dilution. Instructions included with the kit can include, where appropriate, instructions for dilution.

In other aspects, the kits can include pre-mixed compositions and instructions for solubilizing any precipitate that may have formed during shipping or storage. Kits containing solutions of Compound I, or a pharmaceutically acceptable salt thereof, and one or more carriers, excipients or vehicles may also contain any of the materials mentioned above (e.g., any device to aid in preparing the composition for administration or in the administration per se). The instructions in these kits may describe suitable indications (e.g., a description of patients amenable to treatment) and instructions for administering the solution to a patient.

In one aspect, an article of manufacture is disclosed. The article of manufacture may comprise a container comprising a label; and a composition comprising an oxime or pharmaceutically acceptable salt thereof, such as, for example, MMB4, 2-PAM, pralidoxime, HI6, HLo7, and pharmaceutically acceptable salts thereof. In one aspect, the oxime may be MMB4. The label may indicate that the composition is to be administered to an individual prior to and/or during a surgical procedure.

EXAMPLES

Example 1 demonstrates a phrenic nerve-diaphragm preparation useful for detecting test articles that strengthen, weaken, or change minimally force of contraction. Without intending to be limited by theory, the stimulatory portion of the biphasic effect with MMB4 DMS is likely a direct inhibitory effect on AChE. Since the addition of an AChE inhibitor (neostigmine) partially rescued MMB4 DMS when contraction amplitude was reduced by 50%, the blockage observed at higher doses is not believed to be the result of desensitization due to persistent depolarization and is believed to be due to nicotinic antagonism, either at the receptor or receptor linked ion gate channel level. This effect has been observed with 2-PAM, considered a reference drug used to develop the model.

In Example 2, a rabbit model was developed and verified to detect changes in diaphragmatic and skeletal muscle function as well as in systemic/left-ventricular hemodynamics. This in vivo/in situ rabbit preparation was shown to be both stable and responsive to independent cardiovascular/ neuro-muscular changes triggered by either verapamil or cisatracurium, using a negative and positive control, and can be used to detect effects of administration of oximes, such as MMB4 DMS.

Example 1. Action of MMB4 DMS on Neuromuscular Transmission in the Rat and Rabbit Diaphragm In Situ Preparation Applicant investigated model development and assessed neuromuscular (diaphragmatic and skeletal), pulmonary, and cardiovascular alterations to determine effects of administration of both MMB4 DMS and a clinically-relevant comparator (oxime), pralidoxime chloride (2-PAM). Overall, isofluraneanesthetized mechanically-ventilated anesthetized rabbits were instrumented to detect changes in diaphragmatic and skeletal muscle function as well as in systemic/left-ventricular hemodynamics. This in vivo/in situ rabbit preparation was shown to be both stable (for up to 8 hours) and responsive to independent cardio-vascular/neuro-muscular changes triggered by either verapamil or cisatracurium, Therefore, this preparation could be leveraged to detect effects following the administration of mimes.

Applicant sought to extend ex vivo observations from MMB4 DMS when given to isolated phrenic nerve-diaphragm preparations to the in vivo setting, in order to provide clinically relevant information regarding the mechanism(s) of action/effects of MMB4 DMS. Ex vivo experiments showed that MMB4 DMS, when given in a tissue bath, could directly suppress diaphragm contractility at high concentrations. Applicant previously established and validated an in vivo/in situ anesthetized/ventilated rat preparation, demonstrating the effects of 2-PAM on diaphragmatic function (depression).

Applicant's investigation sought to determine the optimal experimental preparation/conditions in rabbits, including 1) an anesthetic regimen capable of providing both adequate surgical-depth anesthesia/analgesia and cardiovascular stability without suppressing centrally-driven spontaneous diaphragmatic contractions, and 2) a repeatable diaphragmatic/skeletal instrumentation/stimulation paradigm.

In addition, experiments were performed to demonstrate the preparation's ability to detect independent skeletal striatal muscle/diaphragmatic and/or cardiovascular alterations. For this purpose, the responses to either 1) a non-depolarizing skeletal muscle relaxant (cisatracurium) to confirm striatal muscle effects, 2) a cardiac channel blocker (verapamil) resulting in cardiovascular dysfunction, as well as 3) time-controlled experiments (to determine any time-dependent changes) were assessed.

Anesthesia/Analgesia:

Animals were sedated/anesthetized with fentanyl (5 pg/kg IV bolus) and ketamine (10 mg/kg IV bolus). Following endotracheal intubation, a surgical plane of anesthesia, necessary for the cardiovascular and neuromuscular instrumentation, was reached via continuous IV infusions of fentanyl (45 pg/kg/hr) and ketamine (9 mg/kg/hr) given in conjunction with inhaled isoflurane (1.5 to 2.5%) delivered in 100% O2 via a positive pressure small animal ventilator (set at approximately 30-35 breaths/min at 30-35 mL/breath, with a 1:2 inspiratory to expiratory ratio). For this model, a combination of partial intravenous anesthesia/analgesia (fentanyl/ketamine) and an inhaled agent (isoflurane) was used, providing both cardiovascular/respiratory stability and, in alignment with the study/model objectives, spontaneous respiratory drive.

Following surgical instrumentation, an experimental plane of anesthesia was maintained via continuous IV infusions of fentanyl (25 pg/kg/hr) and ketamine (9 mg/kg/hr) given in conjunction with inhaled isoflurane (0.9 to 1.1%) delivered in 100% O2. To allow adequate fluid maintenance/balance, the maintenance fentanyl concentration was adjusted via a crystalloid-dilution, targeting a fluid rate of approximately 4 mL/kg/hr over the course of the experiment.

To elicit centrally-driven diaphragmatic contractions (under anesthesia and mechanical ventilation), ventilator support was reduced to about 20 to 25 breaths/min with a tidal volume of 20 to 25 mL/breath. To sustain adequate oxygenation but yield elevated end tidal CO2 values (~50 mmHg). Notably, in this setting, diaphragmatic contractions were completely inhibited when the phrenic nerve was sectioned, confirming the clinically relevant central/intrinsic nature of the induced respiration; in all cases, diaphragmatic contractions were observed when the distal (from the level of de-centralization) phrenic nerve was electrically stimulated.

The inhalant-based anesthetic regimen used (fentanyl/ketamine/isoflurane), proved (for the purposes of the study) superior to a total intravenous propofol-based anesthetic regimen (fentanyl/ketamine/propofol). In this preparation, propofol administration was associated with marked respiratory depression, requiring marked reductions in tidal volume (15 to 20 mL/breath, resulting in higher end tidal CO2 values) to elicit intrinsic diaphragmatic contractions. These observations are in line with the reported respiratory inhibition of propofol (Kashiwagi et al., 2004; Zhang et al. 2009), as well as with an isoflurane-mediated preservation of diaphragmatic contractility (Pavlidou et al., 2013)

Instrumentation:

During anesthesia, core temperature (e.g., via a rectal temperature probe), a single-lead ECG (lead II), and pulse oximetry were monitored. Left-ventricle (LV) pressures were recorded with a high-fidelity micro-manometer catheter that was advanced into the LV retrograde across the aortic valve. Arterial pressures were recorded with a fluid filled catheter that was advanced into the femoral artery. Intra-tracheal peak pressures (ITP) were monitored via a pressure transducer connected to the tracheal tube; given the mechanically-assisted (fixed tidal-volume) ventilation, such pressures can be used as a surrogate of static pulmonary stiffness.

Subsequently, the diaphragm was exposed through a thoracotomy, and a silk-suture was threaded through the diaphragm (from the cranial side) and placed adjacent to the phrenic nerve insertion/innervation point. This suture was hooked to a strain gauge to record diaphragmatic contractions. A portion of the phrenic nerve was also carefully isolated and instrumented with a stimulated bipolar nerve electrode, allowing electrical stimulation of the diaphragm. In a few experiments the phrenic nerve was acutely ligated (cranially to the electrode), resulting in the suppression of all spontaneous diaphragmatic contractions (confirming their central-origin). Upon electrical stimulation, diaphragmatic contractions were observed, suggesting intact neuromuscular function.

Similarly, to record skeletal muscle contractions, a silk-suture was threaded around the vastus *intermedius* and connected to a strain gauge. A portion of the sciatic nerve was also carefully isolated and instrumented with a bipolar nerve electrode, allowing electrical skeletal stimulation. Both sets of electrodes were attached to an impulse generator to assess the responsiveness to stimulation-driven contractions.

Results

For these experiments a preparation was considered acceptable, if the following entry criteria was met: 1) cardiovascular, respiratory, and neuro-muscular signals of sufficient quality for interpretation; 2) adequate diaphragmatic (developed force≥g) and skeletal muscle (developed force≥3 g) function at baseline, and 3) normal cardiac physiology (mean systemic pressures>50 mmHg, $dP/dt_{max}$>1500 mmHg/s, and heart rate≥200 but <350 bpm).

Overall, twelve out of fifteen preparations (i.e., 80%) met these entry criteria with failure rates of 13.3% and 6.7% for the skeletal and diaphragmatic instrumentation. The cardiovascular state of the valid preparations (2.51±0.05 kg, n=12) at the start of the experiments (i.e., at baseline, see Table 2) were considered to be within the normal physiological range (for anesthetized rabbits), and in agreement with previously published literature (e.g., Tate et al., 2011).

TABLE 2

Average baseline characteristics of the isoflurane anesthetized in situ/in vivo rabbit preparation.

| | Baseline Characteristics | |
|---|---|---|
| | Parameter (units) | mean ± SEM (CV) |
| Cardiovascular | HR (bpm) | 282 ± 5 (8.0%) |
| | MAP (mmHg)[1] | 66 ± 2 (16.8%) |
| | SAP (mmHg)[1] | 85 ± 3 (14.9%) |
| | DAP (mmHg)[1] | 53 ± 2 (20.9%) |
| | LVEDP (mmHg)[2] | 7.3 ± 0.8 (49.1%) |
| | LVESP (mmHg)[2] | 76 ± 2 (12.6%) |
| | $LVdP/dt_{max}$ (mmHg/s)[2] | 2819 ± 150 (25.0%) |
| | $LVdP/dt_{min}$ (mmHg/s)[2] | −2841 ± 122 (20.2%) |
| | tau (ms)[2] | 8.5 ± 0.2 (9.2%) |
| NM | Diaphragmatic Force (g)[3] | 32.2 ± 2.8 (39.9%) |
| | Skeletal Force (g)[3] | 7.6 ± 0.6 (35.2%) |
| | ITP (mmHg)[4] | 13.0 ± 0.5 (16.1%) |

Data are mean ± standard error of the mean, with coefficients of variability (CV), shown in parenthesis.
[1]Mean (MAP), systolic (SAP), and diastolic (DAP) Arterial Pressures derived from the systemic arterial pressure signal.
[2]Left-ventricular end-diastolic (LVEDP) and end-systolic pressures (LVESP), as well as the peak rates of pressure change during systole ($LVdP/dt_{max}$)/diastole ($LVdP/dt_{min}$) and the time-constant of left-ventricular relaxation (tau) were derived from the the left-ventricular pressure signal.
[3]Diaphragmatic and skeletal developed forces were derived from calibrated strain-gage force transducers attached to either the diaphragm or to the vastus intermedius (respectively).
[4]Intra-tracheal pressures (peak inspiratory under positive-pressure mechanical ventilation), a surrogate of static respiratory stiffness (given than the tidal volume is fixed).

In these preparations, signals of sufficient quality for interpretation were obtained from the target systems; representative cardiovascular, diaphragmatic/skeletal, and respiratory signals are shown in FIG. 1.

Figure 2:
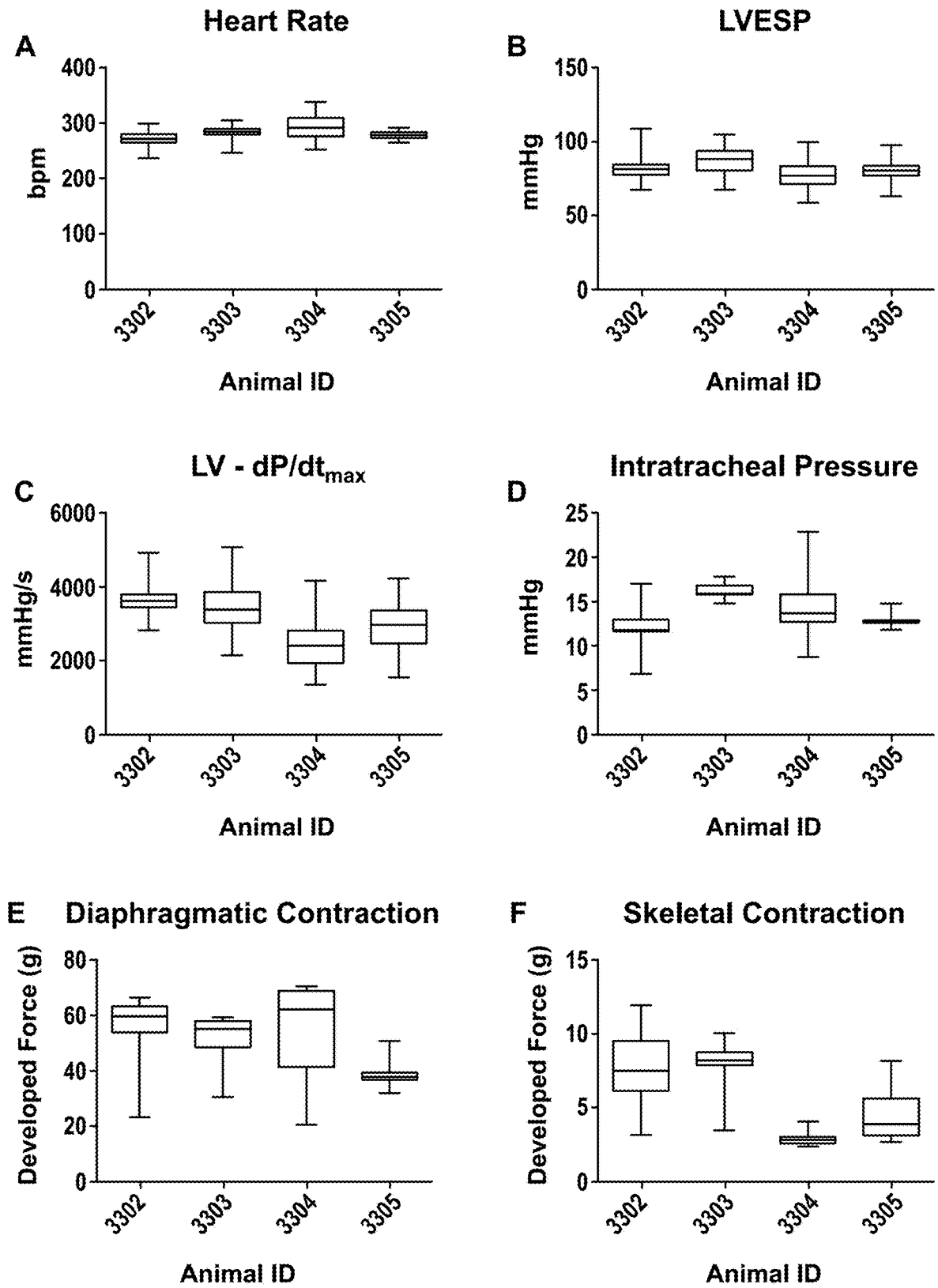
FIG. 2 depicts box plots summarizing the data from the 8-hr time-control experiments (n=4), showing both intra- and inter-animal variabilities expected for both cardiovascular, neuro-muscular, and/or respiratory parameters: A) heart rate, B) end-systolic left ventricular pressure (LVESP), C) the left-ventricular $dP/dt_{max}$, D) the intratracheal pressure, as well as both E) diaphragmatic and F) skeletal muscle contraction over 8 hours.
Figure 3:
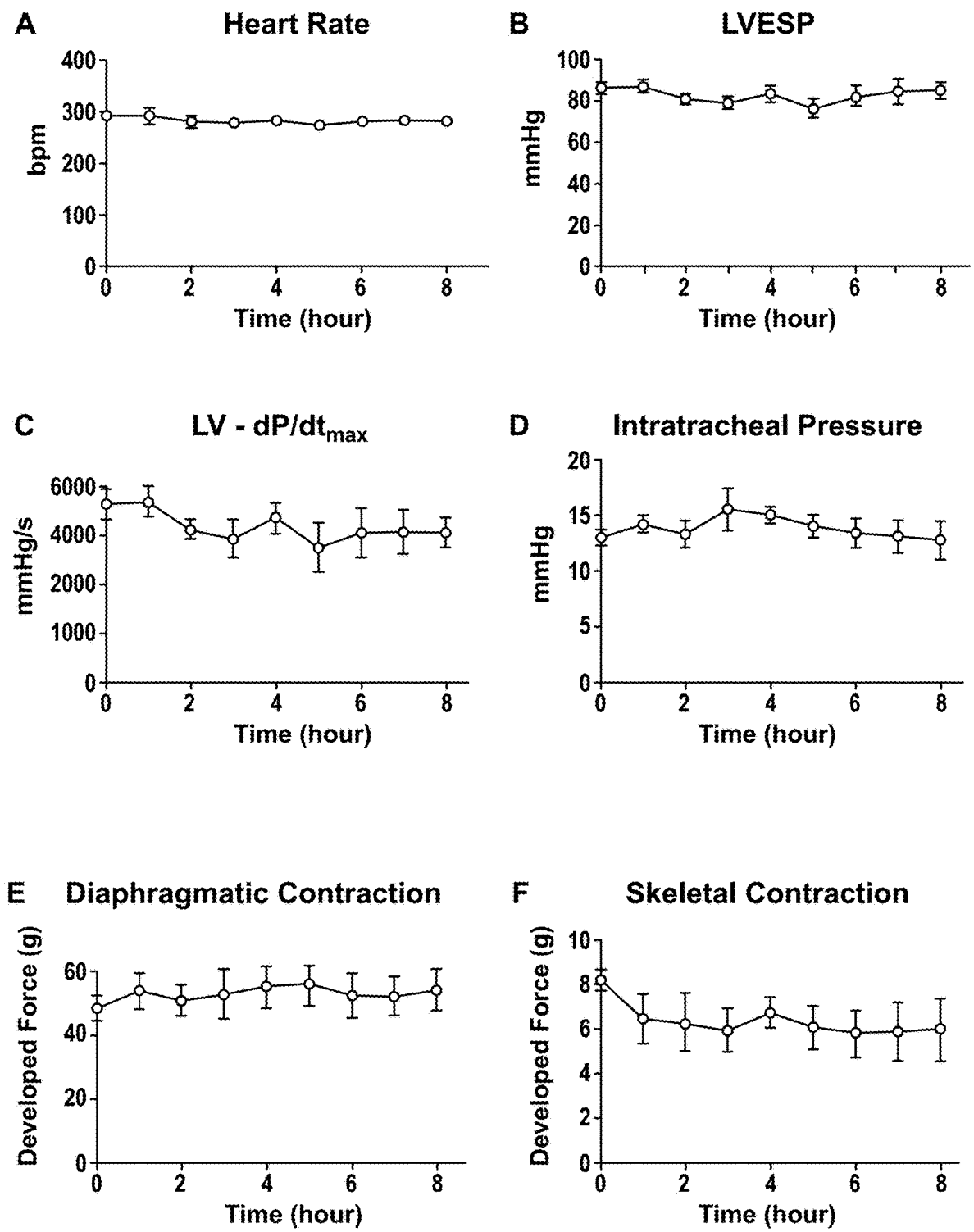
FIG. 3 depicts representative data (means with standard errors) from the time-control experiments (n=4), showing changes over time for cardiovascular, neuro-muscular and/or respiratory parameters: A) heart rate, B) end-systolic left ventricular pressure (LVESP), C) the left-ventricular dP/dt-max, D) the intratracheal pressure, as well as both E) diaphragmatic and F) skeletal muscle contraction over 8 hours.

To establish the natural time-course of the preparation, time-control experiments, where the preparation was followed for up to 8 hours, were conducted. In these experiments, both skeletal and diaphragmatic muscles were electrically stimulated every 20 minutes (for 2-minute bouts), to both avoid muscle fatigue and to delineate between central and neuro-muscular defects. The results of these experiments are summarized in FIGS. 2 and 3, with representative tracings shown in FIG. 1. Overall, hemodynamics and muscle contractions (whether stimulated or intrinsic) were stable for up to 8 hours (see FIG. 3).

Figure 4:
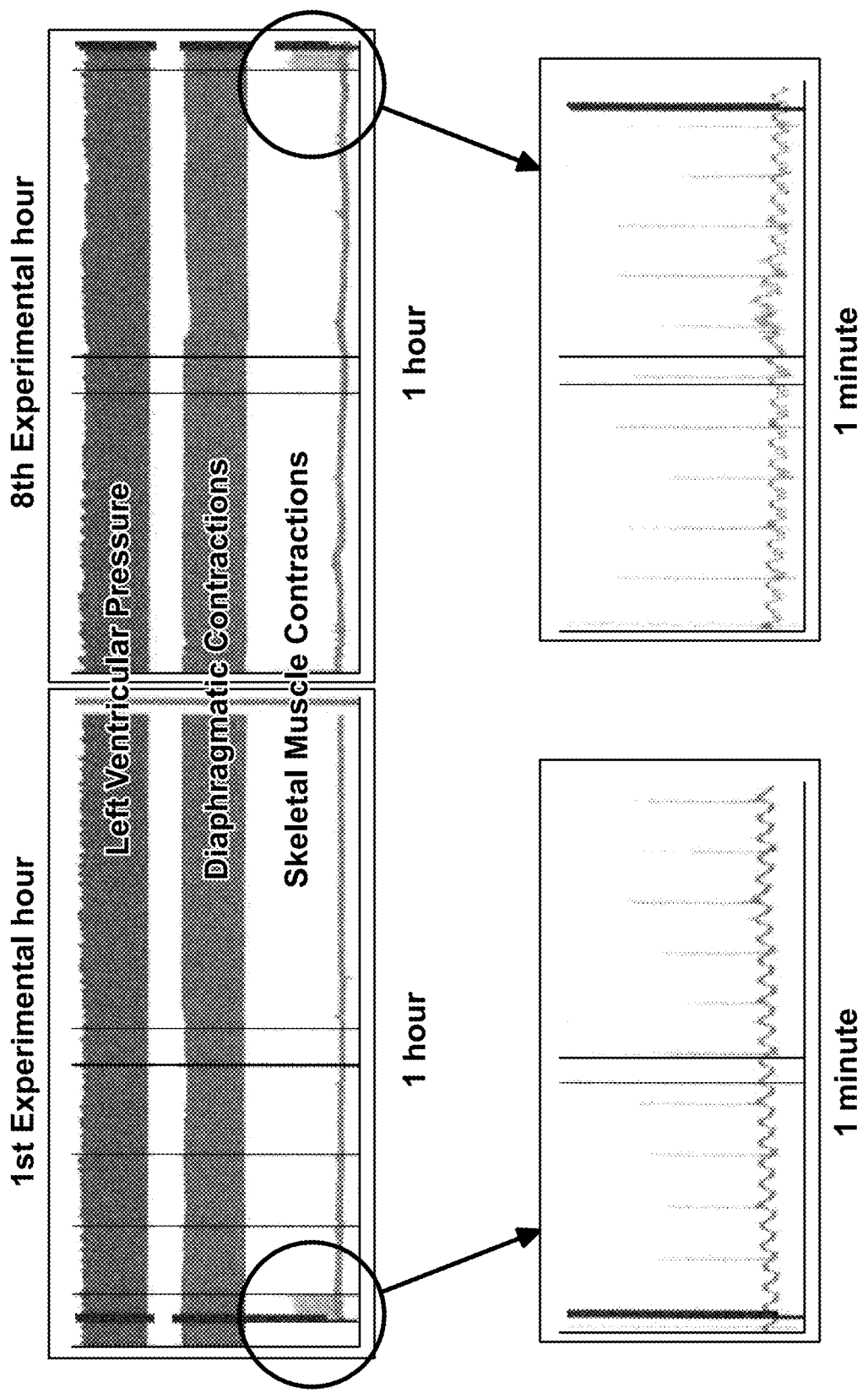
FIG. 4 depicts representative tracings (60 minutes) both at baseline and after 8 hours of time-control in an anesthetized rabbit preparation, showing (top to bottom) left-ventricular pressure (LVP), intrinsic diaphragmatic contraction, and stimulated (insets) skeletal muscle contractions signals.
Figure 5:
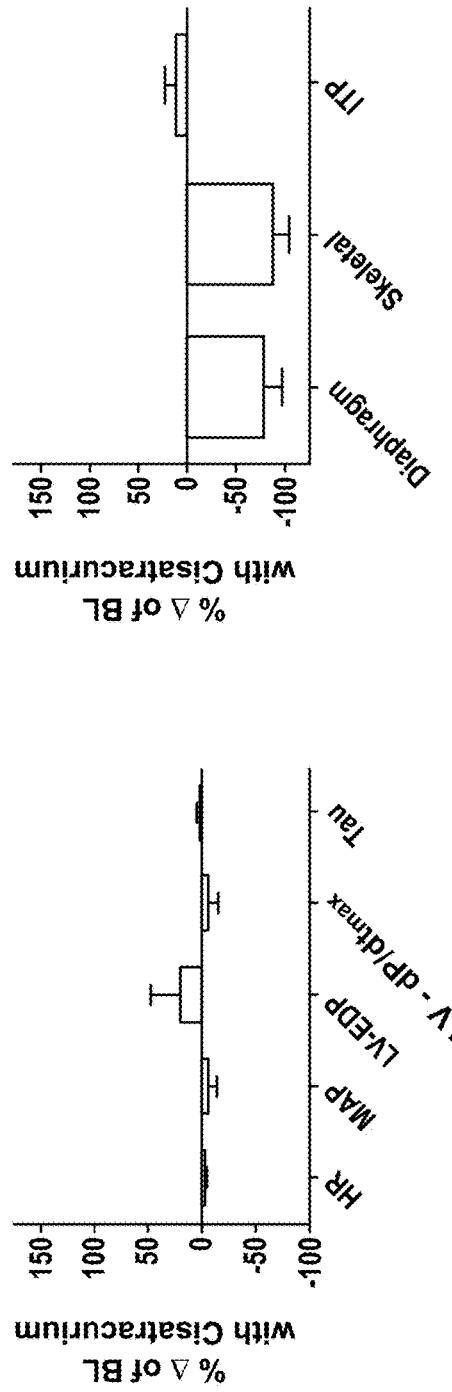
FIG. 5 depicts differential effects of a neuro-muscular blocker (cisatracurium 0.1 to 0.05 mg/kg, n=11; TOP) and a calcium-channel blocker (verapamil 0.6 mg/kg, n=6; BOTTOM) in cardio-vascular (LEFT) and neuromuscular/respiratory parameters (RIGHT); changes (% vs. pre-dosing) in heart rate (HR), mean arterial pressure (MAP), as well as in LV end diastolic pressures (LV-EDP), $dP/dt_{max}$, left-ventricular relaxation time-constant (Tau), diaphragmatic contractions, skeletal contractions, and intratracheal pressure (ITP).
Figure 5:
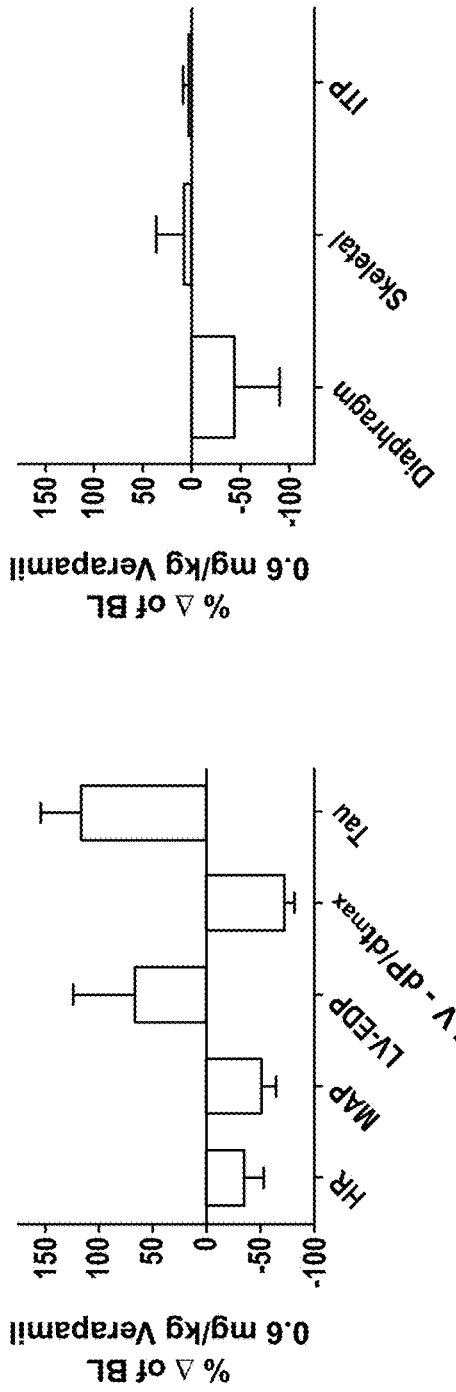

In addition, the experiments showed relatively low intra- and inter-subject variability (see FIG. 4), supporting a power analysis. Based on the intrinsic physiological variability of the data collected from these time-control experiments, the normalized pooled standard deviation (coefficient of variation) for the diaphragmatic force of contraction was 40% (32.2±12.9 g). Hence, a sample size of 8 animals would allow the detection of a 50% reduction in diaphragmatic contraction with a power of 80% at the a-level of 0.05.

Model Responsiveness:

To demonstrate the preparation's ability to assess independent alterations to cardiovascular and/or skeletal striatal/diaphragmatic functions, the responses to either 1) a non-depolarizing muscle relaxant (cisatracurium), or to 2) a toxic dose of a cardiac channel blocker (verapamil) resulting in cardiovascular collapse, were assessed. As expected, verapamil (three 0.2 mg/kg IV boluses) dose-dependently decreased triggered marked cardiovascular alterations (see Table 3 and FIG. 4), decreasing systemic pressures, elevating filling pressures and decreasing indices of both systolic (e.g., dP/dtmax) as well as diastolic cardiac function (slowed tau). Similarly, verapamil moderately depressed diaphragmatic contractions, but had negligible effects in skeletal muscle function (see Table 3 and FIG. 4). These findings are in line with the Ca2+ channel blocker properties of verapamil, and in agreement with the literature (e.g., Su, 1988).

TABLE 3

Acute cardiovascular, neuro-muscular and/or respiratory responses to verapamil given intravenously (three 0.2 mg/kg IV boluses); absolute and relative heart rates (HR), systemic pressures (MAP) and left-ventricular end-diastolic pressures (LVEDP), peak systolic rates of pressure generation (dP/dtmax), and time-constants of relaxation (tau) as well as in both diaphragmatic and skeletal muscle force of contraction before (i.e., at baseline) and following treatment (n = 6).

| Parameter | Verapamil Dose Level (mg/kg)‡ | | | |
|---|---|---|---|---|
| (units) | Baseline | 0.2 (#1) | 0.4 (#2) | 0.6 (#3) |
| HR (bpm) | 280 ± 9 | 255 ± 5 | 252 ± 10 | 188 ± 19 |
| | — | *−9 ± 2* | *−10 ± 3* | *−32 ± 8* |
| MAP (mmHg)[1] | 66 ± 5 | 53 ± 6 | 38 ± 4 | 32 ± 4 |
| | — | *−21 ± 6* | *−42 ± 5* | *−49 ± 6* |
| LVEDP (mmHg)[2] | 8.2 ± 1.6 | 10.4 ± 1.7 | 11.7 ± 1.4 | 11.6 ± 1.6 |
| | — | *33 ± 8* | *67 ± 28* | *71 ± 24* |
| $LVdP/dt_{max}$ (mmHg/s)[2] | 2505 ± 228 | 1418 ± 223 | 836 ± 70 | 640 ± 80 |
| | — | *−45 ± 5* | *−65 ± 4* | *−72 ± 4* |
| tau (ms)[2] | 8.8 ± 0.4 | 12.5 ± 1.2 | 16.7 ± 1.8 | 19.4 ± 1.7 |
| | — | *43 ± 12* | *91 ± 21* | *123 ± 16* |
| Diaphragmatic Force (g)[3] | 21.1 ± 0.9 | 14.8 ± 4.1 | 12.1 ± 3.3 | 11.9 ± 4.8 |
| | — | *−28 ± 19* | *−39 ± 18* | *−38 ± 28* |
| Skeletal Force (g)[3] | 4.5 ± 1.1 | 5.4 ± 1.5 | 5.4 ± 1.6 | 5.9 ± 1.3 |
| | — | *14 ± 8* | *10 ± 14* | *9 ± 12* |
| ITP (mmHg)[4] | 13.9 ± 0.3 | 13.2 ± 0.7 | 14.3 ± 0.7 | 14.3 ± 0.8 |
| | — | *−5 ± 5* | *2 ± 3* | *3 ± 4* |

Data are mean ± standard error of the mean, with relative (%) changes from the baseline (BL) in italics.
‡Verapamil was as three (3) IV bolus injections of 0.2 mg/kg.
[1]Mean (MAP) arterial Pressures from the systemic arterial pressure signal.
[2]Left-ventricular end-diastolic (LVEDP) as well as the peak rate of pressure change during systole ($LVdP/dt_{max}$) and the time-constant of left-ventricular relaxation (tau) were derived from the the left-ventricular pressure signal.
[3]Diaphragmatic and skeletal developed forces were derived from calibrated strain-gage force transducers attached to either the diaphragm or to the vastus intermedius (respectively).
[4]Intra-tracheal pressures (peak inspiratory under positive-pressure mechanical ventilation), a surrogate of static respiratory stiffness (given than the tidal volume is fixed).

Figure 6:
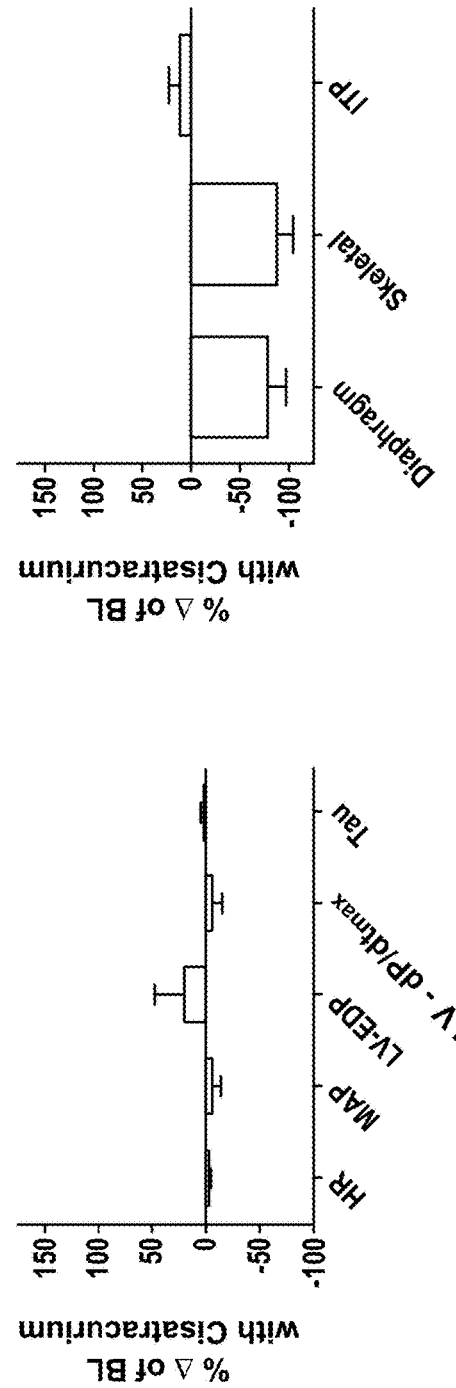
FIG. 6 depicts differential effects of a neuro-muscular blocker (cisatracurium 0.1 to 0.05 mg/kg, n=11; TOP) and a calcium-channel blocker (verapamil 0.6 mg/kg, n=6; BOTTOM) in cardio-vascular (LEFT) and neuromuscular/respiratory parameters (RIGHT); changes (% vs. pre-dosing) in heart rate (HR), mean arterial pressure (MAP), as well as in LV end diastolic pressures (LV-EDP), $dP/dt_{max}$, left-ventricular relaxation time-constant (Tau), diaphragmatic contractions, skeletal contractions, and intratracheal pressure (ITP).
Figure 6:
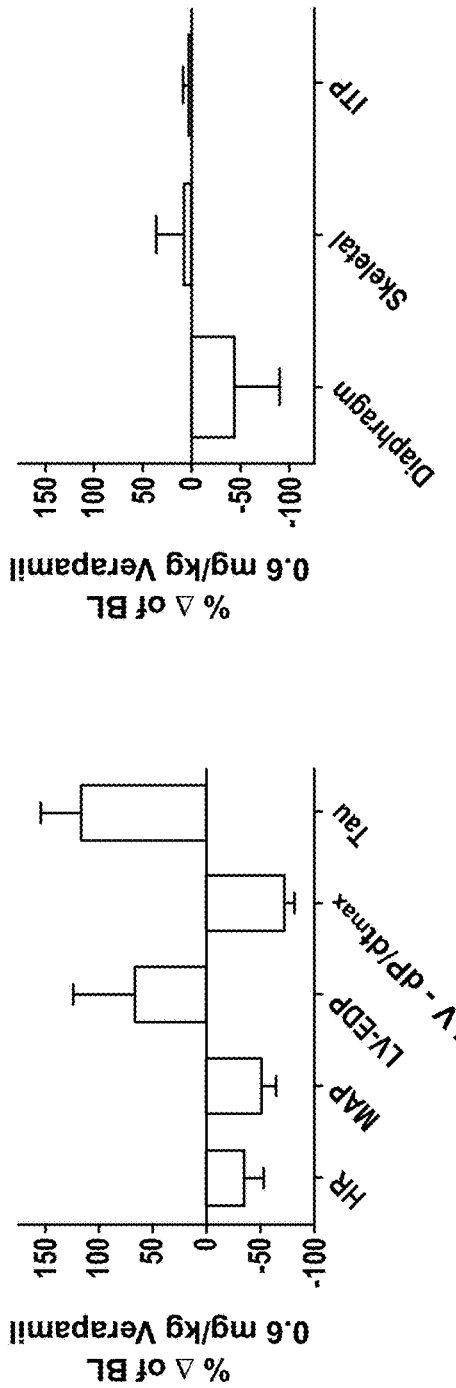
Figure 7:
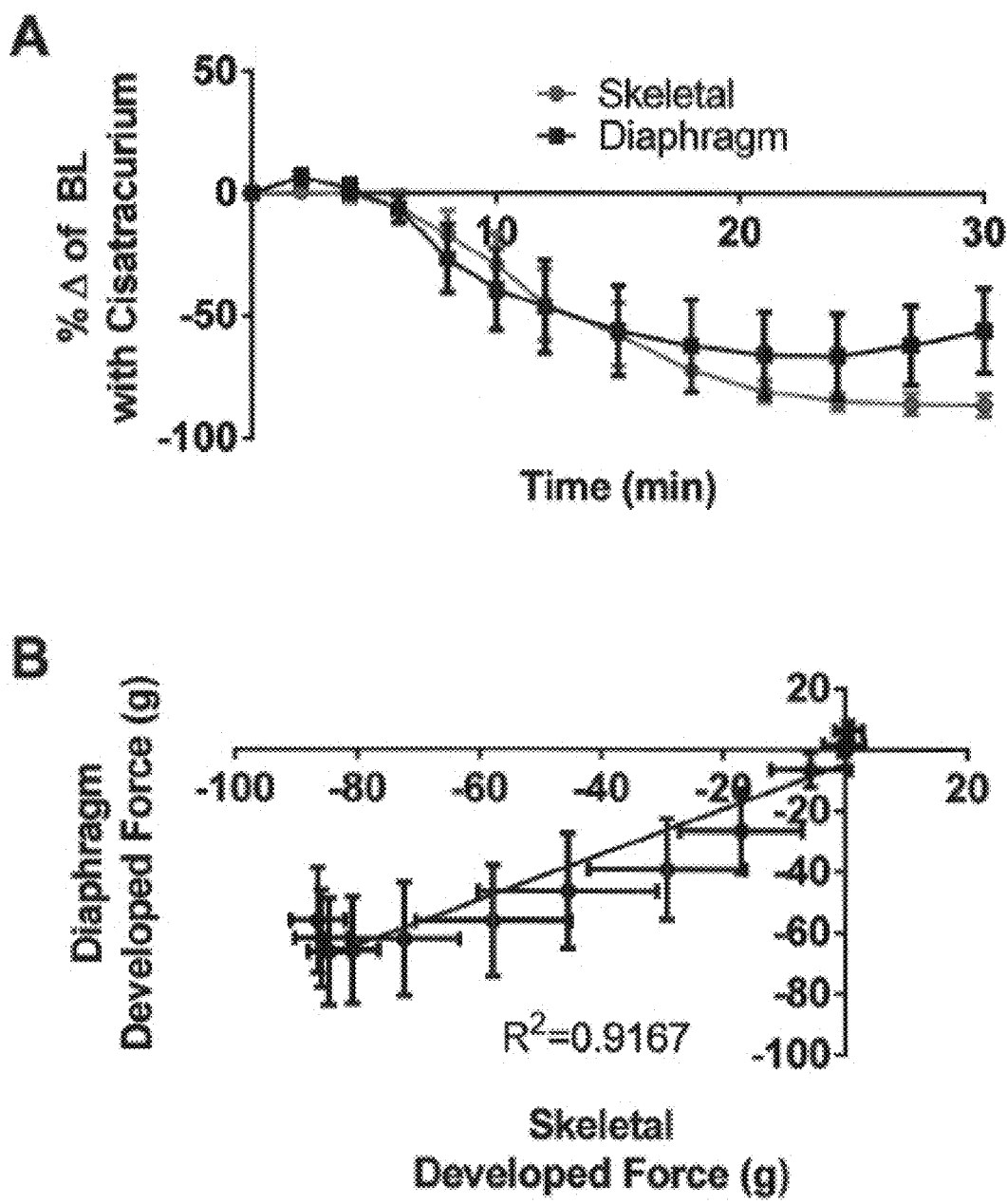
FIG. 7 depicts relative functional time-/dose-dependent depression of cisatracurium (2 ug/kg/min IV for 30 min, n=11) on both diaphragmatic and skeletal muscle force (A, top). B) Estimated relationship (and linear approximation) between the observed skeletal and diaphragmatic depressions triggered by cisatracurium.

On the other hand, cisatracurium when administered as either a bolus (0.1 mg/kg IV) or as an infusion (2 ug/kg/min for 30 minutes, resulted in the reversible inhibition of skeletal and diaphragmatic contractions but had negligible effects in cardiovascular function (see Table 4 and FIGS. 6 and 7). Moreover, for this non-depolarizing neuromuscular blocking agent, the data suggest a similar rate of inhibition/functional depression for both diaphragm and skeletal muscle, suggesting that changes in neuromuscular skeletal function may be valid clinical surrogate for diaphragmatic depression. Indeed, cisatracurium-induced changes in skeletal muscle function were a good ($R^2$=0.91) linear prediction of diaphragmatic inhibition (see FIG. 4), however, it tended to over-/under-estimate diaphragmatic depression at both low/high concentrations (i.e., onset/offset of infusion).

TABLE 4

Acute cardiovascular, neuro-muscular and/or respiratory
responses to cisatracurium given intravenously (either as a bolus: 0.1
mg/kg IV or as an infusion: 2 ug/kg/min for 30 min); absolute and
relative heart rates (HR), systemic pressures (MAP) and left-
ventricular end-diastolic pressures (LVEDP), peak systolic rates of
pressure generation (dP/dtmax), and time-constants of relaxation (tau)
as well as in both diaphragmatic and skeletal muscle force of
contraction before (i.e., at baseline) and following treatment
(n = 11).

|  | Cisatracurium (μg/kg)‡ | |
| --- | --- | --- |
| Parameter (units) | Baseline | 100 or 50 |
| HR (bpm) | 283 ± 7 | 282 ± 7 |
|  | — | *0 ± 1* |
| MAP (mmHg)[1] | 64 ± 5 | 63 ± 6 |
|  | — | *−3 ± 3* |
| LVEDP (mmHg)[2] | 6.8 ± 1.1 | 7.6 ± 1.1 |
|  | — | *17 ± 8* |
| LVdP/dt$_{max}$ (mmHg/s)[2] | 2894 ± 203 | 2760 ± 246 |
|  | — | *−6 ± 3* |
| tau (ms)[2] | 8.7 ± 0.2 | 8.7 ± 0.2 |
|  | — | *0 ± 1* |
| Diaphragmatic Force (g)[3] | 24.9 ± 3.7 | 5.4 ± 1.0 |
|  | — | *−77 ± 6* |
| Skeletal Force (g)[3] | 7.9 ± 1.1 | 1.1 ± 0.5 |
|  | — | *−86 ± 5* |
| ITP (mmHg)[4] | 14.2 ± 0.4 | 15.1 ± 0.6 |
|  | — | *7 ± 4* |

Data are mean ± standard error of the mean, with relative (%) changes from the baseline (BL) in italics.
‡cisatracurium given either as a bolus (0.1 mg/kg IV) or as an infusion (2 μg/kg/min IV for 25 min).
[1]Mean (MAP) arterial Pressures from the systemic arterial pressure signal.
[2]Left-ventricular end-diastolic (LVEDP) as well as the peak rate of pressure change during systole (LVdP/dt$_{max}$) and the time-constant of left-ventricular relaxation (tau) were derived from the the left-ventricular pressure signal.
[3]Diaphragmatic and skeletal developed forces were derived from calibrated strain-gage force transducers attached to either the diaphragm or to the vastus intermedius (respectively).
[4]Intra-tracheal pressures (peak inspiratory under positive-pressure mechanical ventilation), a surrogate of static respiratory stiffness (given than the tidal volume is fixed).

Taken together these results/observations demonstrate an in vivo isoflurane anesthetized mechanically-ventilated anesthetized rabbit model capable of detecting neuromuscular (diaphragmatic and skeletal) and cardiovascular alterations in situ. The rabbit preparation was shown to be both stable and responsive to independent cardiovascular/neuromuscular changes triggered by either verapamil or cisatracurium, making it useful for detecting effects of oxime administration.

Example 2. Action of MMB4 DMS on
Neuromuscular Transmission in an In Vitro Rat
Phrenic Nerve-Diaphragm Muscle Preparation Applicant developed a rat phrenic nerve-diaphragm preparation and assessed the effects of MMB4 DMS on contraction amplitude and potential neuromuscular junction suppression. Using a phrenic nerve-diaphragm muscle preparation, a functional assessment measuring diaphragm muscle contraction was evaluated. A time control to determine stability of the model was evaluated by continuous stimulation measuring for up to 3 hours. An acetylcholinesterase inhibitor (neostigmine) and nicotinic cholinergic receptor agonist (nicotine) served as positive controls for muscle stimulation; while the nicotinic acetylcholine receptor antagonist (d-tubocurarine chloride) served as positive control for muscle inhibition. Muscarine, a muscarinic cholinergic receptor agonist, served as the negative control for muscle stimulation. The same procedure was done with MMB4 DMS (10-7 to 10-2 M) in separate settings; 1) alone, 2) alone without stimulation or 3) during a 50% reduction with d-tubocurarine. Additionally, an ancillary purpose was to determine if function could be modulated with addition of neostigmine. A dose response of sodium methanesulfonate was also assessed at similar concentration of MMB4 DMS. For each preparation, baseline was collected for 60 minutes prior to dosing. The vertical, phrenic nerve-diaphragm preparation successfully detected test articles that strengthen, weaken, or change minimally force of contraction. The stimulatory portion of the biphasic effect with MMB4 DMS is likely a direct inhibitory effect on AChE. Since the addition of an AChE inhibitor (neostigmine) partially rescued MMB4 DMS when contraction amplitude was reduced by 50%, the blockage observed at higher doses is not the result of desensitization due to persistent depolarization and likely due to nicotinic antagonism, either at the receptor or receptor linked ion gate channel level. As SMS did not elicit a functional effect, the functional effect of MMB4 is not believed to be due to the counter ion, DMS.

MMB4 DMS is an oxime that has the potential to reactivate nerve agent-inhibited AChE in the peripheral tissues. Receptor binding data indicate that MMB4 DMS displaces radioligand binding to human nicotinic end plate receptors and choline transporters in a dose-dependent manner (Table 5). The functional consequence, if any, of this displacement is unknown. Applicant has found that Methylenebis {4-[(hydroxyimino) methyl]-pyridinium}dimethanesulfonate (MM4B DMS), can potentially reactivate acetylcholinesterase (AChE) and/or have a direct agonistic effect on the nicotinic receptor in the peripheral tissues following exposure to nerve agents. Receptor binding data indicate that MMB4 DMS displaces nicotinic receptors and choline transporters in a dose-dependent manner

TABLE 5

MMB4 DMS-Dependent Radioligand Binding Percent Displacement

| MMB4 DMS | Radioligand Binding % Displacement | |
| --- | --- | --- |
| Concentration | Nicotinic End Plate Receptor | Choline Transporter |
| 50 μM | 40% | — |
| 250 μM | 61% | 61% |
| 1,000 μM | 72% | 83% |

Test Compounds

Test Article: MMB4 DMS (Methylenebis{4-[(hydroxyimino) methyl]-pyridinium}dimethanesulfonate); Formulation: MMB4 DMS was prepared in distilled water and used within 20 days of preparation; Concentrations: The test article was formulated into concentrations of 3 mM or 1 M in order to yield target concentrations of 1 pM to 10 mM; Storage Conditions: The test article was stored at room temperature. Lot Number: 1004

Test Reagent: d-tubocurarine chloride hydrate; Formulation: d-tubocurarine was prepared in distilled water and used within 30 days of preparation; Concentrations: The test reagent concentration of 0.3 mM to yield target concentrations of 0.2 pM, 0.5 pM, 1 pM, and 2 pM; Storage Conditions: The test reagent was kept refrigerated at 2 to 8° C.

Test Reagent: (−)-Nicotine detartrate; Formulation: Nicotine was prepared in distilled water and used within 1 day of preparation; Concentrations: The test reagent concentration of 0.09 mM to yield target: concentrations of 0.3 pM, 3 pM and 30 pM; Storage Conditions: The test reagent was stored at room temperature.

Test Reagent: Neostigmine; Formulation: Neostigmine was prepared in distilled water and used within 30 days of preparation; Concentrations: The test reagent concentration of 1 mM to yield target concentrations of 0.5 pM, 2 pM and 5 pM; Storage Conditions: The test reagent was stored at room temperature.

Test Reagent: (±)-Muscarine chloride hydrate (Muscarine); Formulation: Muscarine was prepared in distilled water and used within 30 days of preparation; Concentrations: The test reagent concentration of 1 mM to yield target concentrations of 0.333 pM, 1 pM, 3.33 pM and 10 pM; Storage Conditions: The test reagent was stored at room temperature.

Test Reagent: Sodium Methanesulfonate (SMS); Formulation: Sodium Methanesulfonate was prepared in distilled water and used within 30 days of preparation; Concentrations: The test reagent concentrations of 1 M to yield target concentrations of 10 pM, 100 pM, 1 mM, and 10 mM; Storage Conditions: The test reagent was stored at room temperature.

Bathing Solution: Krebs Solution; Formulation: Krebs solution was formulated per facility SOP 205; Composition: The Krebs solution consisted of the following excipients:

Distilled Water: N/A

Krebs-Henseleit Buffer 9.6 g/L $NaHCO_3$ 2.1 g/L $CaCl_2$ (99%) 0.2 g/L

Storage Conditions: Krebs was stored per manufacturer's instructions. When not in use, the formulated Krebs solution was stored in a refrigerator set to maintain a temperature of 2 to 8° C.

Route of Administration:

All reagents were administered directly into the organ bath containing 30 mL Krebs via pipette.

Study Design:

Using a phrenic nerve-diaphragm muscle preparation, a functional assessment measuring diaphragm muscle contraction was evaluated. A time control to determine stability of the model was evaluated by continuous stimulation measuring for up to 3 hours. The variables were assessed every 15 minutes for the duration of the study. These values were used as time-controls to correct for the time-dependent decrement in contraction in the preparation. To confirm the validity of the experimental setup, controls were studied. An acetylcholinesterase inhibitor (neostigmine) and nicotinic cholinergic receptor agonist (nicotine) served as positive controls for muscle stimulation; while the nicotinic acetylcholine receptor antagonist (d-tubocurarine chloride) served as positive control for muscle inhibition. Muscarine, a muscarinic cholinergic receptor agonist, served as the negative control for muscle stimulation. The same procedure was done with MMB4 DMS (10-7 to 10-2 M) in separate settings; 1) alone, 2) alone without stimulation or 3) during a 50% reduction with d-tubocurarine. Additionally, an ancillary purpose was to determine if function could be modulated with addition of neostigmine. A dose response of sodium methanesulfonate was also assessed at similar concentration of MMB4 DMS. For each preparation, baseline was collected for 60 minutes prior to dosing. Escalating doses of test reagents or articles were pipetted into the organ bath every 15 minutes in cumulative fashion. It should be noted, unlike the other doses, a washout was required between neostigmine doses.

Anesthesia to Harvest Left Nerve-Diaphragm

Rats were anesthetized with ketamine/xylazine combination (−45/−5 mg/kg IP; and with supplemental isoflurane [1 to 3%], if needed via mask), shaved and positioned in dorsal recumbence, endotracheally intubated via a tracheotomy, and ventilated (−90 breaths/min, 2.5 mL tidal volume with 95%/5% [$O_2/CO_2$]) with an adjustable small animal ventilator (Harvard Apparatus). Once a surgical plane of anesthesia was established, (i.e., absent toe pinch reflex), the thoracic cavity was opened and the diaphragm was isolated by cutting laterally below the diaphragm and around the rat's flank. Since the left phrenic nerve is more commonly used in this preparation due to accessibility, only the left nerve was removed. The nerve-diaphragm was removed from the chest and quickly placed in a jacketed dish and was hooked to a water bath containing warmed modified Krebs solution (−37° C.).

3.4.2. Functional Preparation

In the dish, two 3-0 to 4-0 silk sutures were tied to the central connective tissue of the diaphragm and sutured through 2 separate holes in the electrode holder. Another 3-0 to 4-0 silk suture was affixed to the intercostal muscles. The nerve was placed on the electrodes. The holder/muscle-nerve was lifted out of the dish and placed into the organ bath. The vertically attached muscle was pulled taut and securely hung between the two sutures that connected the muscle to the electrode holder and suture through the intercostal muscle that was attached to the strain gauge. Using a tension adjuster, the passive force was set at 1.5 grams. The bath contained Krebs solution gassed with 95%/5% [$O_2/CO_2$] at 37° C. The phrenic nerves were stimulated at 2 V at 0.2 Hz.

Data Analyses:

Data on muscle contractions were acquired digitally (I0×; EMKA Technologies) and analyzed offline. All data records were dated/labeled per QTest Labs standard operating procedures with the study/animal number, and stored in duplicate on separate computers. In all cases, any additional calculations (if required) were performed in spreadsheets (e.g., Microsoft Excel). Data (for all times/groups) are presented as means with standard errors.

Results

Figure 8:
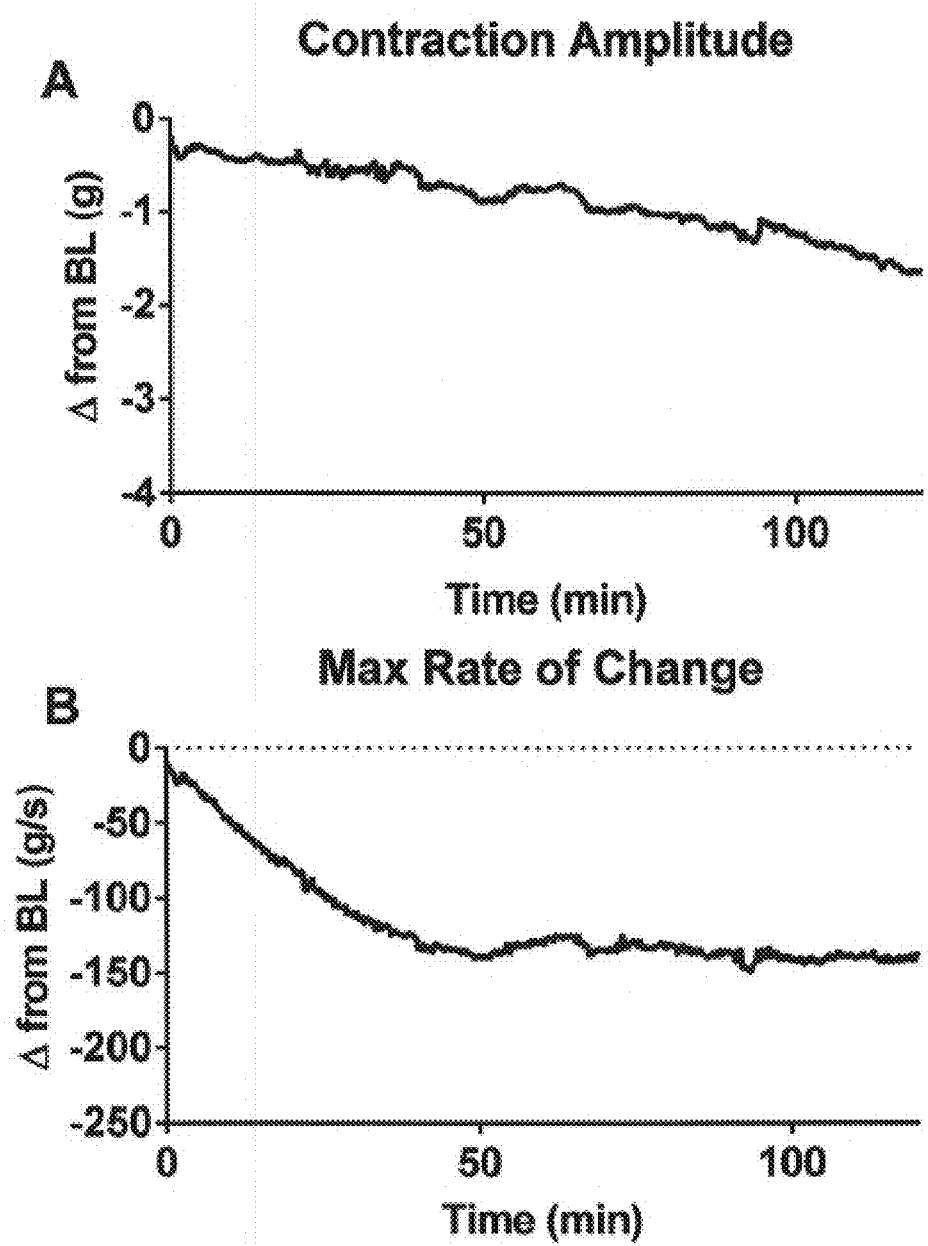
FIG. 8 depicts time controlled traces on (A) contraction amplitude and (B) maximal rate of change in rat left phrenic nerve-diaphragm preparation; represented as mean values±SEM (n=9).

Overall, sixty (60) left phrenic nerve-diaphragm preparations were used. Prior to the assessment of the test article, the preparation was developed and time-controlled experiments (without pharmacological intervention) were first performed to determine the time-dependent decrement in contraction in the preparation (FIG. 8).

Subsequently, both positive and negative controls were used to demonstrate its ability to precisely and accurately measure diaphragmatic contraction via phrenic nerve stimulation. Two (2) end-point parameters were used in the analysis; the muscle contraction amplitude and its maximal rate of rise.

Figure 9:
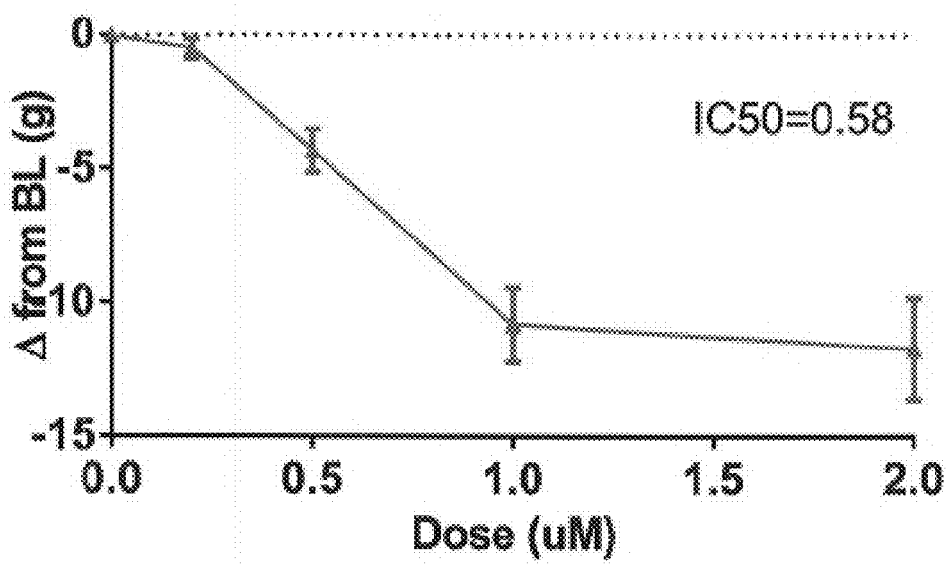
FIG. 9 depicts effects of d-tubocurarine on (A) contraction amplitude and (B) maximal rate of change in rat left phrenic nerve-diaphragm preparation; represented as time controlled adjusted changes from baseline±SEM (n=4).
Figure 9:
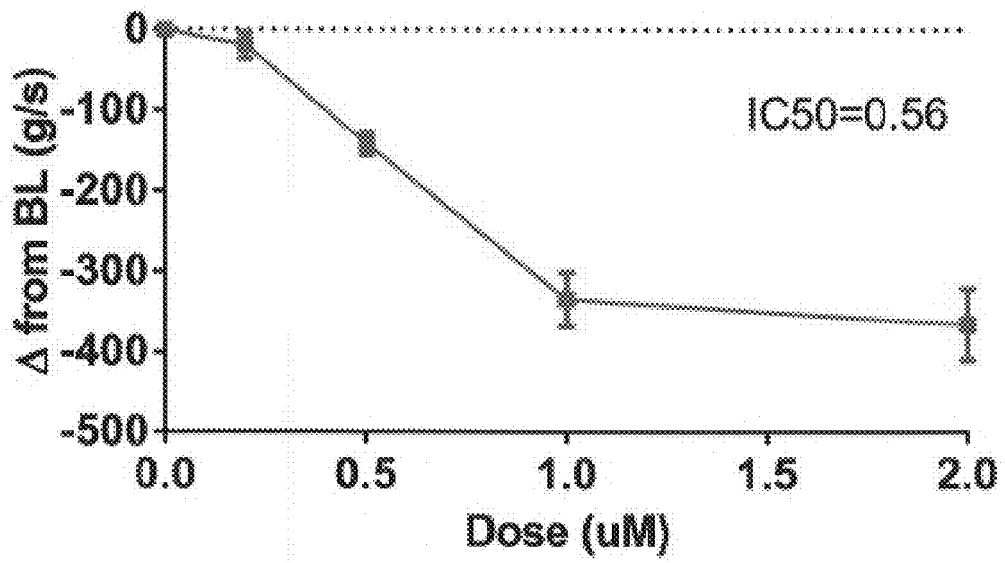

Positive Control for Muscle Inhibition:

To investigate the ability to detect muscle inhibition, d-tubocurarine, a well-established nicotinic cholinergic receptor antagonist, was evaluated. As shown in Table 6 and FIG. 9, d-tubocurarine produced a dose-dependent effect reducing muscle contraction and maximal rate of change with a 50% inhibitory concentration (IC50) of 0.6 pM for muscle contraction and 0.64 pM for maximal rate of change.

TABLE 6

Effects of d-tubocurarine on contraction amplitude and its maximal rate of change in rat left phrenic nerve-diaphragm preparation; represented as raw values and as time controlled adjusted changes from baseline ± SEM (n = 4).

| Dose (μM) | Parameter | d-tubocurarine Raw Values | Δ from BL |
|---|---|---|---|
| Baseline | Contraction Amplitude (g) | 14.6 ± 1.8 | — |
|  | Max Rate of Change (g/s) | 382 ± 45 | — |
| 0.2 | Contraction Amplitude (g) | 14.1 ± 1.8 | −0.5 ± 0.4 |
|  | Max Rate of Change (g/s) | 363 ± 45 | −19 ± 16 |
| 0.5 | Contraction Amplitude (g) | 10.3 ± 1.8 | −4.3 ± 0.8 |
|  | Max Rate of Change (g/s) | 241 ± 49 | −141 ± 14 |
| 1 | Contraction Amplitude (g) | 3.7 ± 0.7 | −10.8 ± 1.4 |
|  | Max Rate of Change (g/s) | 49 ± 18 | −333 ± 33 |
| 2 | Contraction Amplitude (g) | 2.8 ± 0.2 | −11.7 ± 1.9 |
|  | Max Rate of Change (g/s) | 17 ± 5 | −365 ± 44 |

Figure 10:
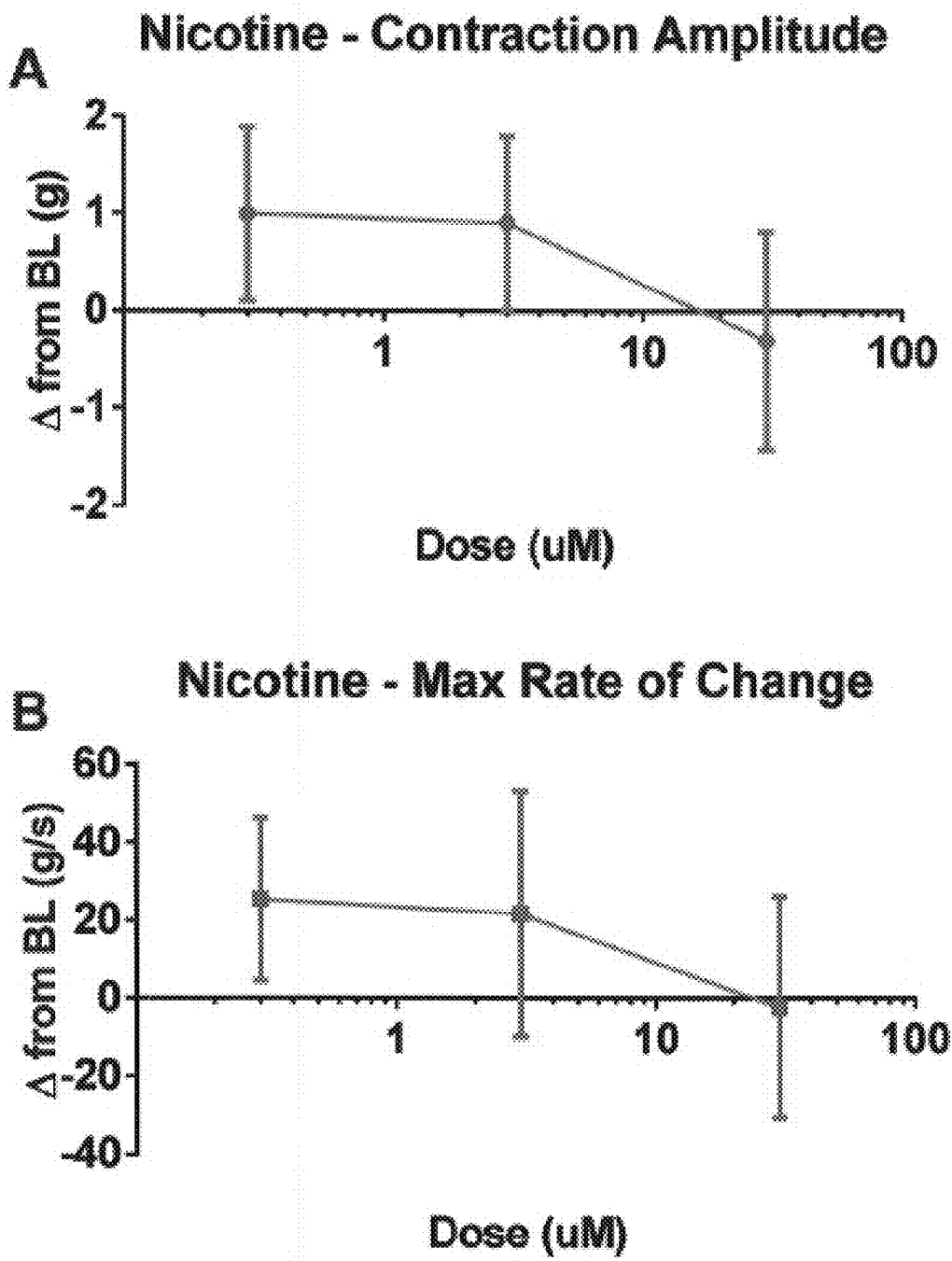
FIG. 10 depicts effects of nicotine on (A) contraction amplitude and (B) maximal rate of change in rat left phrenic nerve-diaphragm preparation; represented as time controlled adjusted changes from baseline±SEM (n=4).

Positive Control for Muscle Stimulation:

To investigate the ability to detect a positive effect on muscle contraction, both nicotine, a nicotinic cholinergic receptor agonist, and neostigmine, an acetylcholinesterase inhibitor, were evaluated. Overall, low doses of nicotine (0.3 and 3 pM) appeared to have a positive effect on contraction and maximal rate of change (Table 7 and FIG. 10).

TABLE 7

Effects of nicotine on contraction amplitude and its maximal rate of change in rat left phrenic nerve-diaphragm preparation; represented as raw values and as time controlled adjusted changes from baseline ± SEM (n = 3).

| Dose (μM) | Parameter | Nicotine Raw Values | Δ from BL |
|---|---|---|---|
| Baseline | Contraction Amplitude (g) | 10.0 ± 3.1 | — |
|  | Max Rate of Change (g/s) | 203 ± 78 | — |
| 0.3 | Contraction Amplitude (g) | 11.0 ± 3.4 | 1.0 ± 0.4 |
|  | Max Rate of Change (g/s) | 229 ± 97 | 25 ± 21 |
| 3 | Contraction Amplitude (g) | 10.8 ± 3.2 | 0.9 ± 0.4 |
|  | Max Rate of Change (g/s) | 225 ± 102 | 22 ± 32 |
| 30 | Contraction Amplitude (g) | 9.7 ± 2.6 | −0.3 ± 0.5 |
|  | Max Rate of Change (g/s) | 201 ± 94 | −2 ± 28 |

Figure 11:
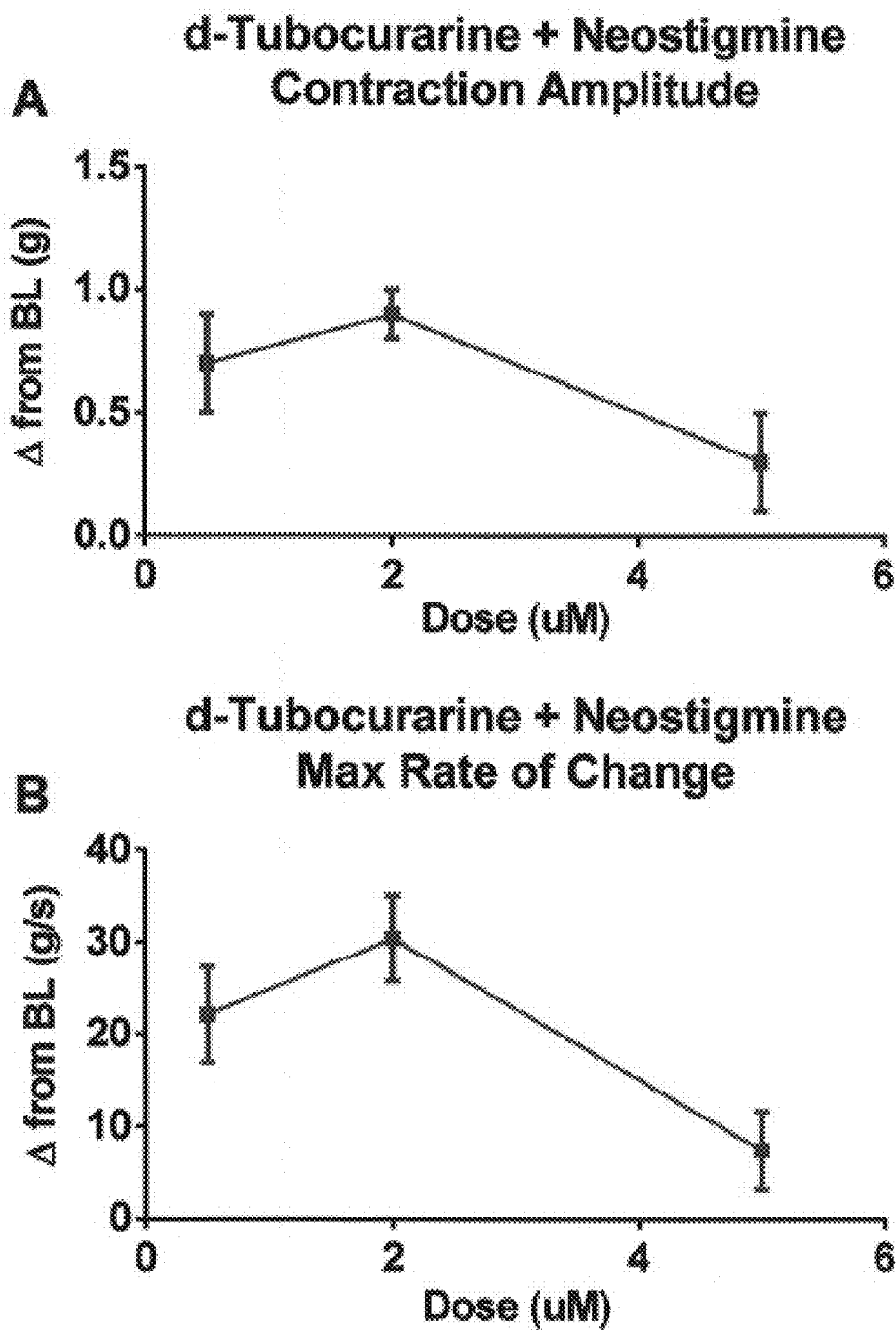
FIG. 11 depicts the effects of neostigmine when added after a 50% reduction with d-tubocurarine on (A) contraction amplitude and (B) maximal rate of change in rat left phrenic nerve-diaphragm preparation; represented as time controlled adjusted changes from baseline±SEM (n=3-10).

However, at the high dose (30 pM), nicotine depressed contraction, most likely due to persistent depolarization. Neostigmine was also assessed, but in a setting where contraction was reduced by −50% with d-tubocurarine. Shown in Table 8 and FIG. 11, at 0.2 and 2 pM, neostigmine increased contraction and maximal rate of change, whereas 5 pM had no effect.

TABLE 8

Effects of neostigmine when added after a 50% reduction with d-tubocurarine on contraction amplitude and its maximal rate of change in rat left phrenic nerve-diaphragm preparation; represented as raw values and as time controlled adjusted changes from baseline ± SEM (n = 3-10).

| Dose (μM) | Parameter | d-tubocurarine Raw Values | Neostigmine with d-tubocurarine Raw Values | Δ from d-tubocurarine |
|---|---|---|---|---|
| 0.5 | Contraction Amplitude (g) | 5.2 ± 0.9 | 5.9 ± 0.8 | 0.7 ± 0.2 |
|  | Max Rate of Change (g/s) | 119 ± 31 | 141 ± 30 | 22 ± 5 |
| 2 | Contraction Amplitude (g) | 4.3 ± 0.5 | 5.2 ± 0.6 | 0.9 ± 0.1 |
|  | Max Rate of Change (g/s) | 101 ± 20 | 131 ± 21 | 30 ± 5 |
| 5 | Contraction Amplitude (g) | 4.4 ± 1.1 | 4.7 ± 1.2 | 0.3 ± 0.2 |
|  | Max Rate of Change (g/s) | 101 ± 35 | 108 ± 39 | 7 ± 4 |

Figure 12:
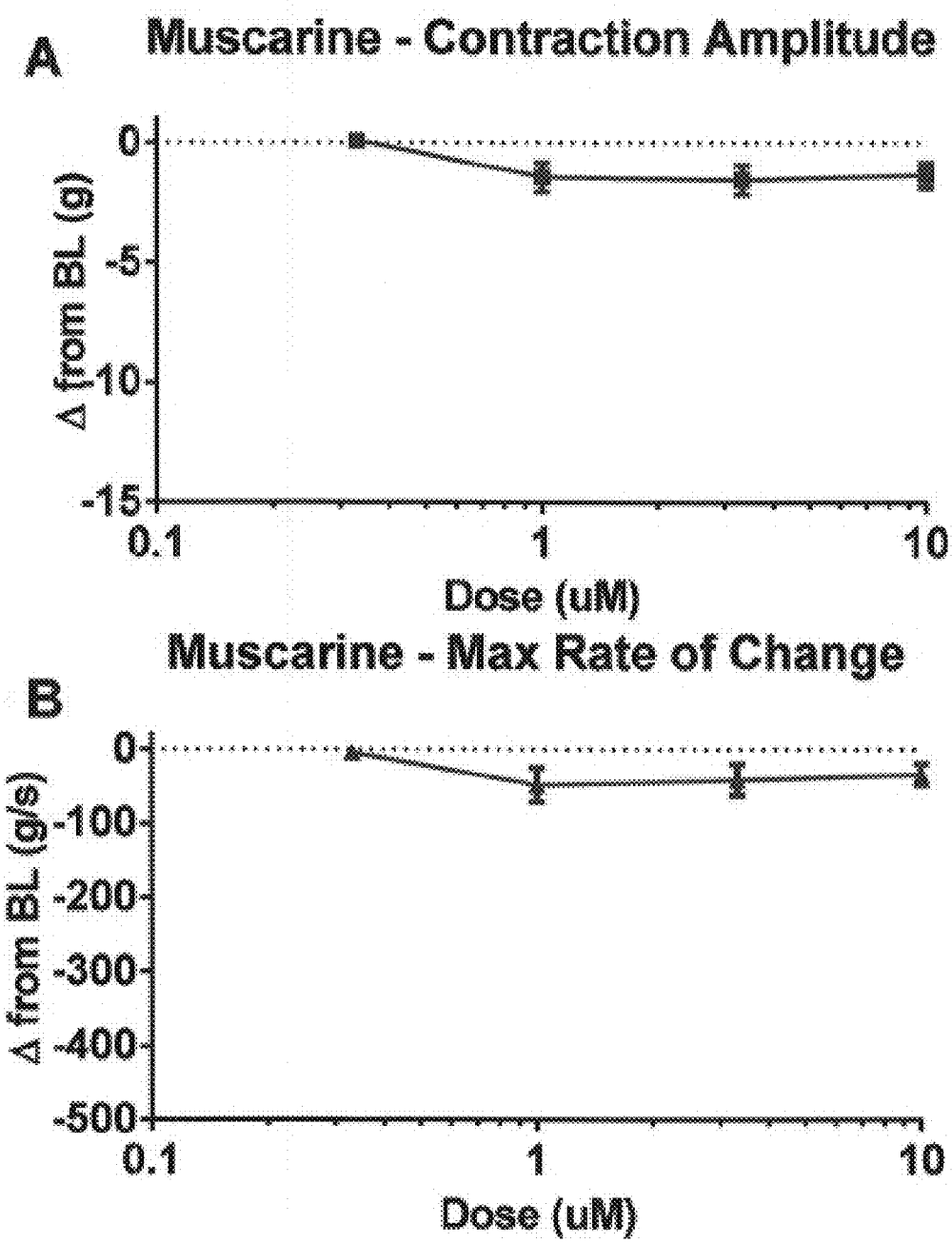
FIG. 12 depicts the effects of muscarine on (A) contraction amplitude and (B) maximal rate of change in rat left phrenic nerve-diaphragm preparation; represented as time controlled adjusted changes from baseline±SEM (n=4).

Negative Control for Muscle Stimulation:

To investigate the absence of an effect on contraction, a muscarinic cholinergic receptor agonist was evaluated. As shown in Table 9 and FIG. 12, muscarine had a minimal or slight reduction of force, and maximal rate of change.

TABLE 9

Effects of muscarine on contraction amplitude and its maximal rate of change in rat left phrenic nerve-diaphragm preparation; represented as raw values and as time controlled adjusted changes from baseline ± SEM (n = 4).

| Dose (μM) | Parameter | Muscarine Raw Values | Δ from BL |
|---|---|---|---|
| Baseline | Contraction Amplitude (g) | 14.8 ± 1.0 | — |
|  | Max Rate of Change (g/s) | 361 ± 32 | — |
| 0.33 | Contraction Amplitude (g) | 14.5 ± 1.4 | 0.1 ± 0.1 |
|  | Max Rate of Change (g/s) | 341 ± 45 | −4 ± 6 |
| 1 | Contraction Amplitude (g) | 13.5 ± 1.2 | −1.4 ± 0.6 |
|  | Max Rate of Change (g/s) | 314 ± 45 | −47 ± 23 |
| 3.33 | Contraction Amplitude (g) | 13.3 ± 1.2 | −1.5 ± 0.6 |
|  | Max Rate of Change (g/s) | 321 ± 41 | −40 ± 21 |
| 10 | Contraction Amplitude (g) | 13.5 ± 1.3 | −1.3 ± 0.5 |
|  | Max Rate of Change (g/s) | 329 ± 39 | −33 ± 14 |

Figure 13:
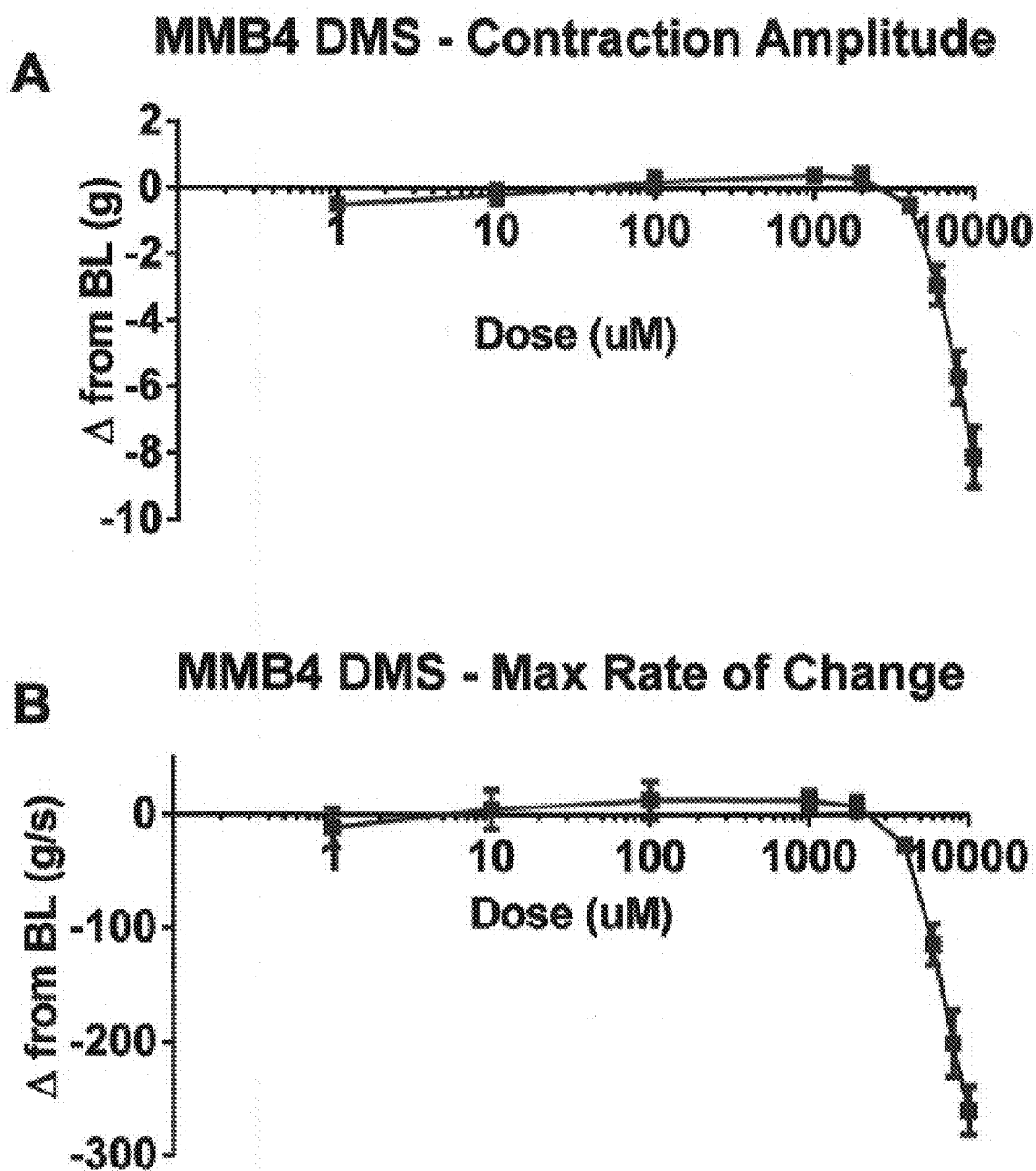
FIG. 13 depicts the effects of MMB4 DMS on (A) contraction amplitude and (B) maximal rate of change in rat left phrenic nerve-diaphragm preparation; represented as time controlled adjusted changes from baseline±SEM (n=4-9).

MMB4 DMS Assessment:

To determine the effect of MMB4 DMS on the neuromuscular junction in the in vitro rat phrenic nerve-diaphragm muscle preparation, doses ranging between 1 pM and 10 mM were assessed. Shown in Table 10 and FIG. 13, MMB4 DMS produced a dose dependent effect.

TABLE 10

Effects of MMB4 DMS on contraction amplitude and its maximal rate of change in rat left phrenic nerve-diaphragm preparation; represented as raw values and as time controlled adjusted changes from baseline ± SEM (n = 4-9).

| Dose (μM) | Parameter | MMB4 DMS Raw Values | Δ from BL |
|---|---|---|---|
| Baseline | Contraction Amplitude (g) | 10.3 ± 0.9 | — |
|  | Max Rate of Change (g/s) | 236 ± 26 | — |
| 1 | Contraction Amplitude (g) | 10.0 ± 1.1 | −0.5 ± 0.2 |
|  | Max Rate of Change (g/s) | 194 ± 37 | −12 ± 17 |
| 10 | Contraction Amplitude (g) | 10.3 ± 0.9 | −0.2 ± 0.3 |
|  | Max Rate of Change (g/s) | 238 ± 29 | 4 ± 17 |

TABLE 10-continued

Effects of MMB4 DMS on contraction amplitude and its maximal rate of change in rat left phrenic nerve-diaphragm preparation; represented as raw values and as time controlled adjusted changes from baseline ± SEM (n = 4-9).

| | | MMB4 DMS | |
|---|---|---|---|
| Dose (μM) | Parameter | Raw Values | Δ from BL |
| 100 | Contraction Amplitude (g) | 10.5 ± 1.0 | 0.2 ± 0.3 |
| | Max Rate of Change (g/s) | 256 ± 32 | 13 ± 16 |
| 1000 | Contraction Amplitude (g) | 10.2 ± 0.9 | 0.4 ± 0.2 |
| | Max Rate of Change (g/s) | 269 ± 32 | 14 ± 8 |
| 2000 | Contraction Amplitude (g) | 7.9 ± 1.6 | 0.3 ± 0.3 |
| | Max Rate of Change (g/s) | 207 ± 45 | 7 ± 9 |
| 4000 | Contraction Amplitude (g) | 7.2 ± 1.4 | −0.5 ± 0.2 |
| | Max Rate of Change (g/s) | 178 ± 37 | −27 ± 7 |
| 6000 | Contraction Amplitude (g) | 5.1 ± 1.0 | −2.9 ± 0.6 |
| | Max Rate of Change (g/s) | 103 ± 23 | −115 ± 18 |
| 8000 | Contraction Amplitude (g) | 2.8 ± 0.6 | −5.7 ± 0.8 |
| | Max Rate of Change (g/s) | 29 ± 9 | −202 ± 30 |
| 10000 | Contraction Amplitude (g) | 3.2 ± 0.8 | −8.1 ± 0.9 |
| | Max Rate of Change (g/s) | 35 ± 14 | −260 ± 21 |

Figure 14:
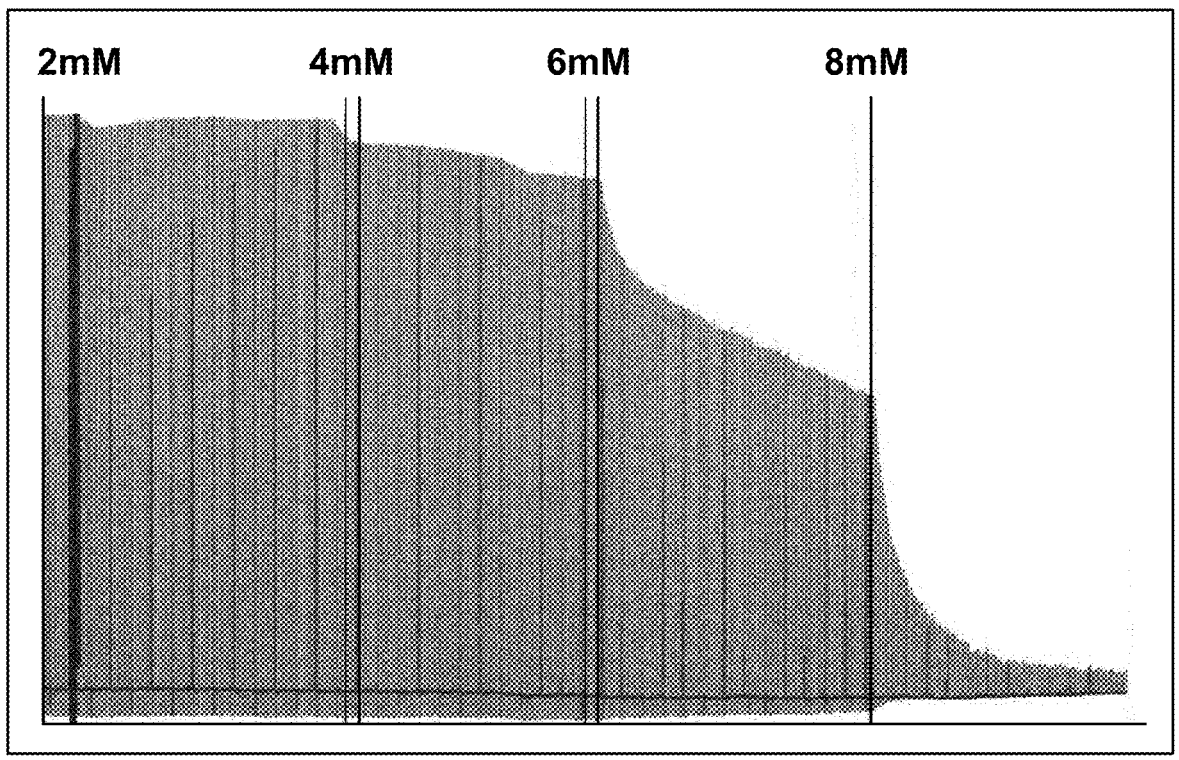
FIG. 14 depicts a representative trace of 2, 4, 6 and 8 mM MMB4 DMS with 15 minutes in between doses in rat left phrenic nerve-diaphragm preparation.

For instance, MMB4 DMS had negligible effect at low doses (1-100 uM), a stimulatory effect at 1 and 2 mM, an inhibitor effect from 4 to 8 mM, and complete blockade of muscle contraction and maximal rate of change at 10 mM. The dose response of 2, 4, 6, and 8 mM MMB4 DMS is shown in FIG. 14.

Figure 15:
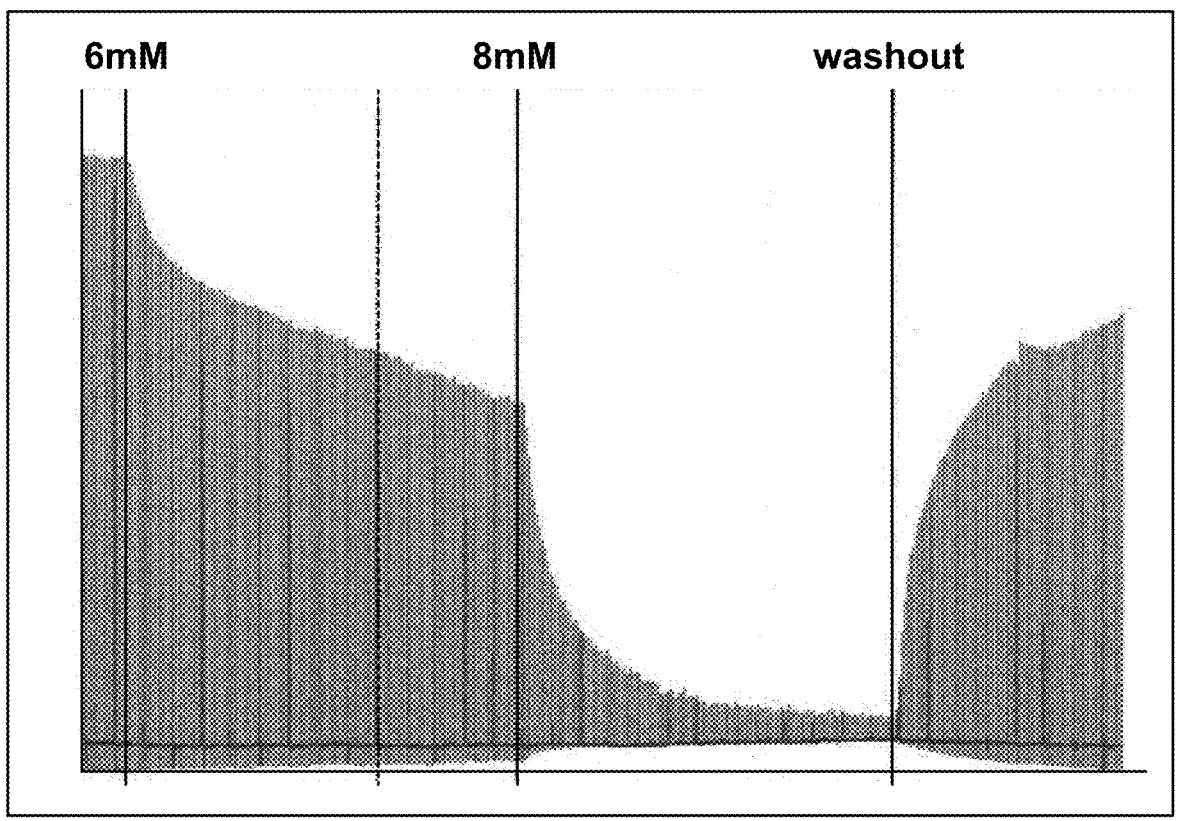
FIG. 15 depicts a representative trace of a washout of 8 mM MMB4 DMS in rat left phrenic nerve-diaphragm preparation.
Figure 16:
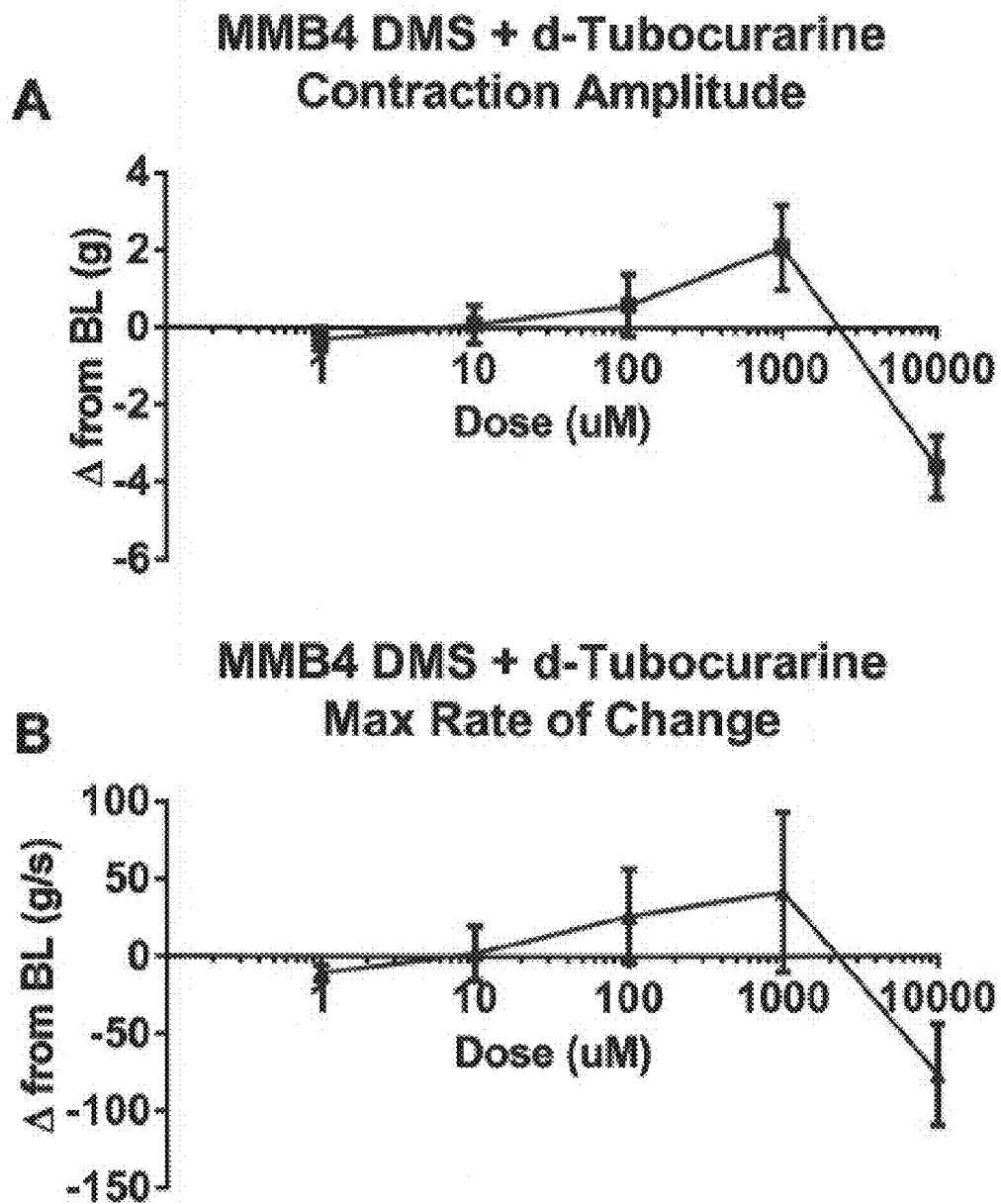
FIG. 16 depicts the effects of MMB4 DMS when added after a 50% reduction with d-tubocurarine on (A) contraction amplitude and (B) maximal rate of change in rat left phrenic nerve-diaphragm preparation; represented as time controlled adjusted changes from baseline±SEM (n=6-9).

Upon washout, contraction amplitude was restored (representative shown in FIG. 15), suggesting the neuromuscular blockade with MMB4 DMS is reversible. The IC50 was 6.2 mM for muscle contraction and 6.4 mM for maximal rate of change. MMB4 DMS elicited a similar effect on muscle contraction following a 50% reduction in contraction amplitude with d-tubocurarine (Table 11 and FIG. 16).

TABLE 11

Effects of MMB4 DMS when added after a 50% reduction with d-tubocurarine on contraction amplitude and its maximal rate of change in rat left phrenic nerve-diaphragm preparation; represented as raw values and as time controlled adjusted changes from baseline ± SEM (n = 6-9).

| | | MMB4 DMS | |
|---|---|---|---|
| Dose (μM) | Parameter | Raw Values | Δ from 50% reduction with d-tubocurarine |
| 50% reduction with d-tubocurarine | Contraction Amplitude (g) | 5.2 ± 0.8 | — |
| | Max Rate of Change (g/s) | 106 ± 22 | — |
| 1 | Contraction Amplitude (g) | 4.1 ± 1.2 | −0.3 ± 0.3 |
| | Max Rate of Change (g/s) | 79 ± 45 | −10 ± 5 |
| 10 | Contraction Amplitude (g) | 5.4 ± 1.0 | 0.1 ± 0.5 |
| | Max Rate of Change (g/s) | 98 ± 32 | 2 ± 18 |
| 100 | Contraction Amplitude (g) | 5.9 ± 1.5 | 0.6 ± 0.8 |
| | Max Rate of Change (g/s) | 146 ± 48 | 26 ± 30 |
| 1000 | Contraction Amplitude (g) | 8.0 ± 1.8 | 2.1 ± 1.1 |
| | Max Rate of Change (g/s) | 187 ± 55 | 42 ± 52 |
| 10000 | Contraction Amplitude (g) | 2.2 ± 0.4 | −3.6 ± 0.8 |
| | Max Rate of Change (g/s) | 25 ± 2 | −76 ± 33 |

Figure 17:
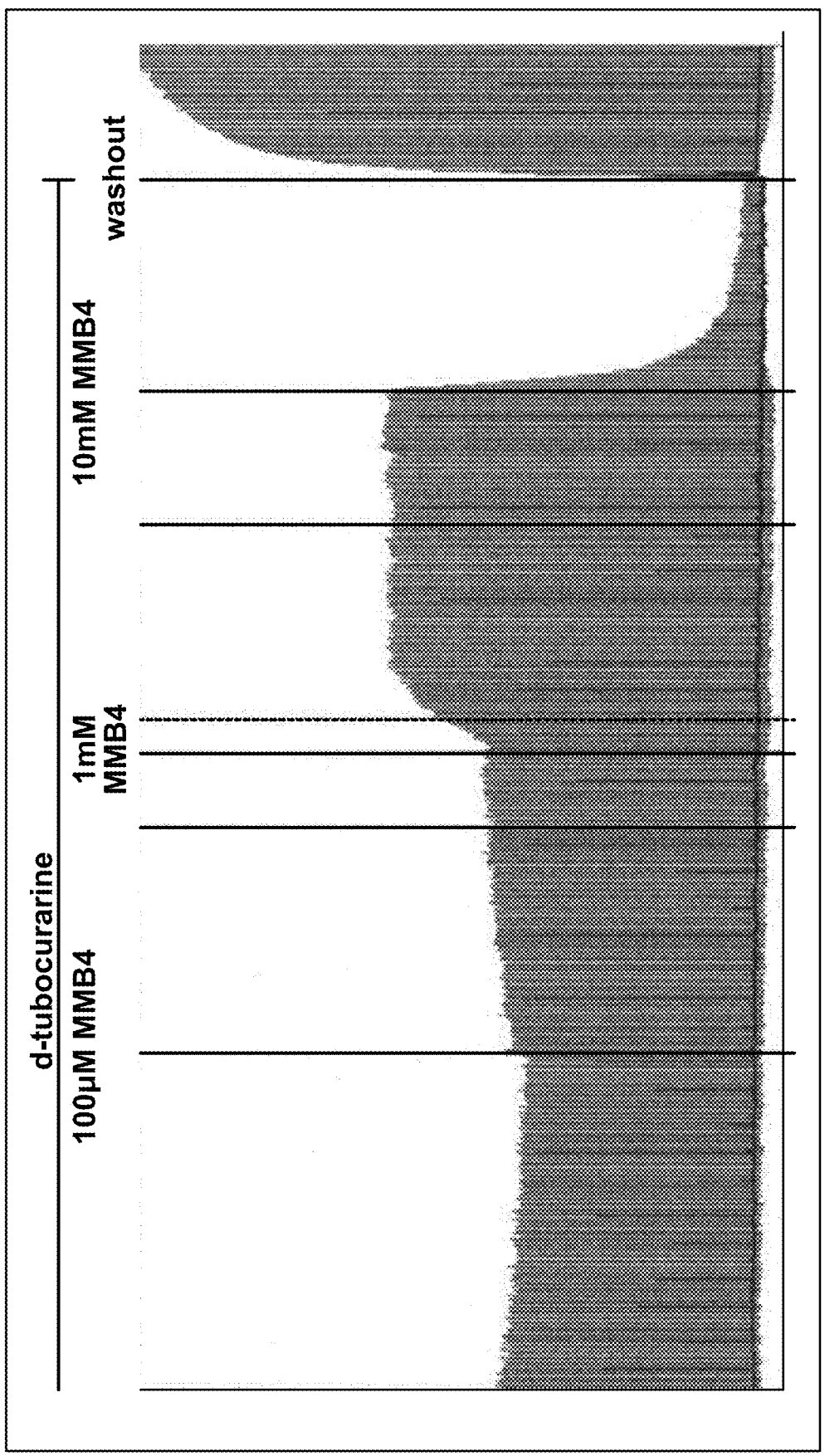
FIG. 17 depicts a representative trace of the stimulatory effect of 100 pM and 1 mM MMB4 DMS after a 50% reduction in muscle contraction amplitude with d-tubocurarine, the neuromuscular blockade with 10 mM MMB4 DMS, and washout of MMB4 DMS and d-tubocurarine with 15 minutes in between doses in rat left phrenic nerve-diaphragm preparation.

That is, there was a biphasic effect of MMB4, specifically, a stimulatory effect was observed at 100 pM and 1 mM, and a complete blockade at 10 mM (representative trace in FIG. 17).

Figure 18:
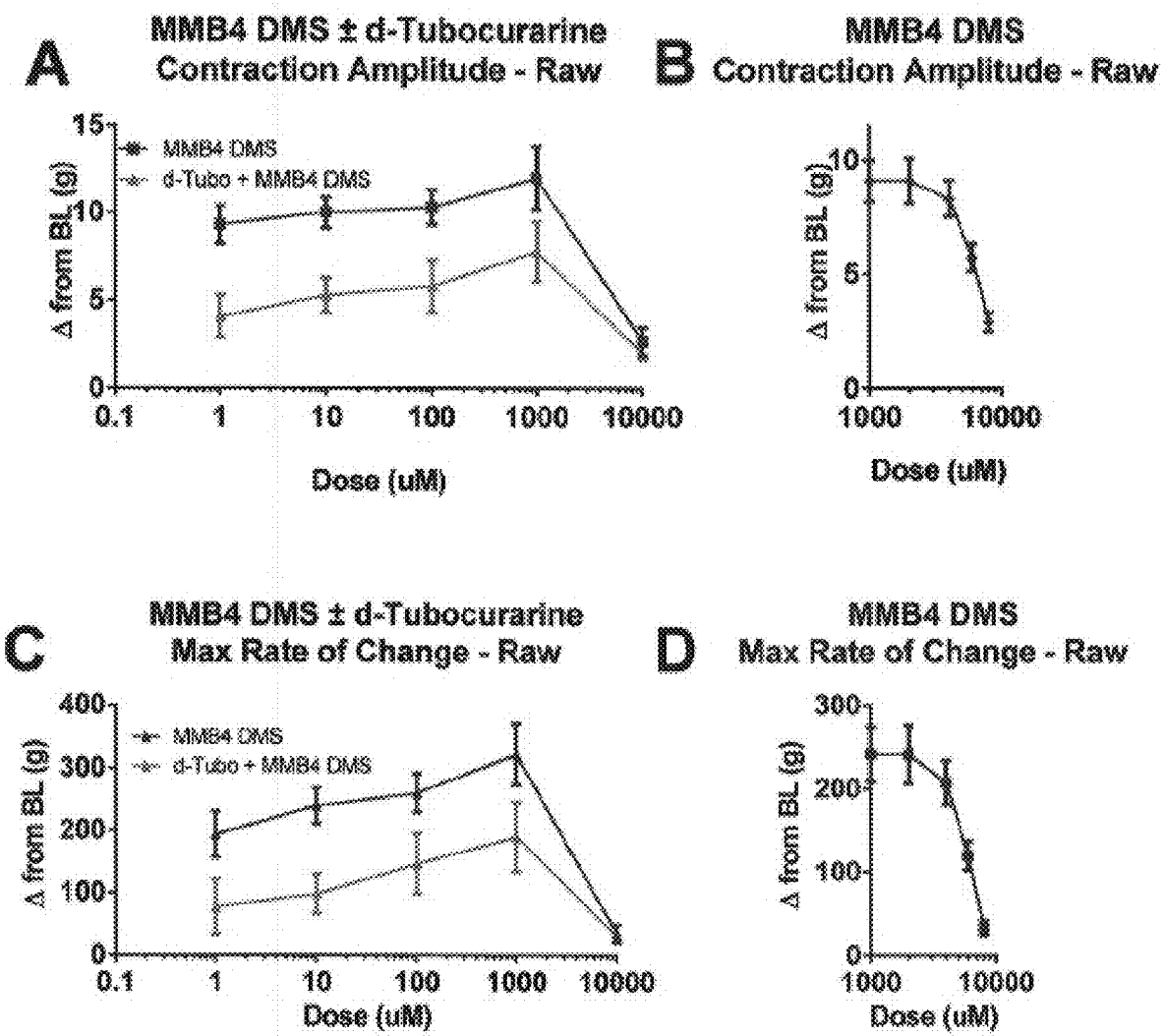
FIG. 18 depicts the effects of MMB4 DMS alone and when added after a 50% reduction with d-tubocurarine on (A-B) contraction amplitude and (C-D) maximal rate of change performed at separate times (A and C performed first, B and D performed second) in rat left phrenic nerve diaphragm preparation; represented as time controlled adjusted mean values±SEM (n=6-9).

With high doses (i.e., 10 mM) of MMB4 DMS (alone or following d-tubocurarine inhibition), contraction amplitude and maximal rate of change fell to a similar level (raw values shown in FIG. 18).

Figure 19:
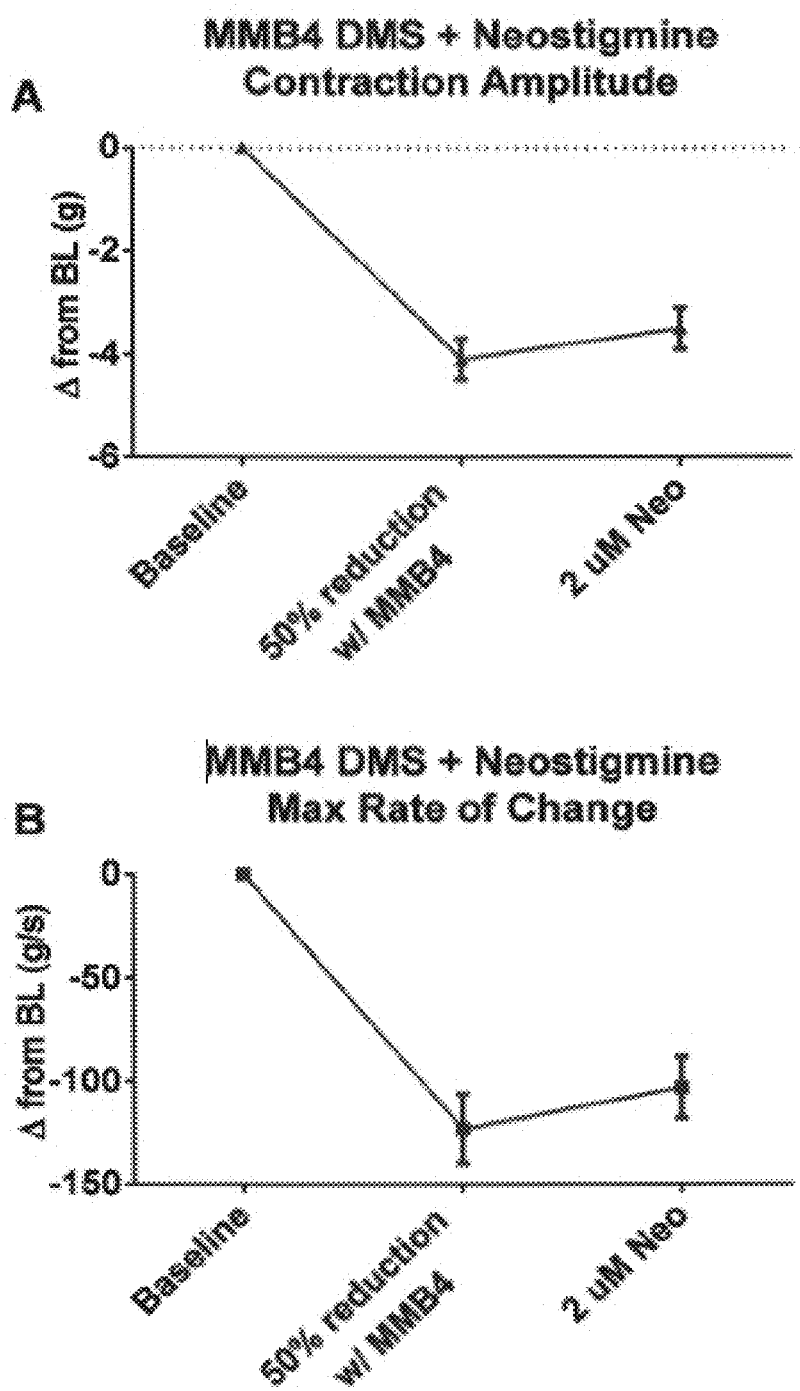
FIG. 19 depicts the effects of neostigmine when added after a 50% reduction with MMB4 DMS on (A) contraction amplitude and (B) maximal rate of change in rat left phrenic nerve-diaphragm preparation; represented as time changes from baseline±SEM (n=4).
Figure 20:
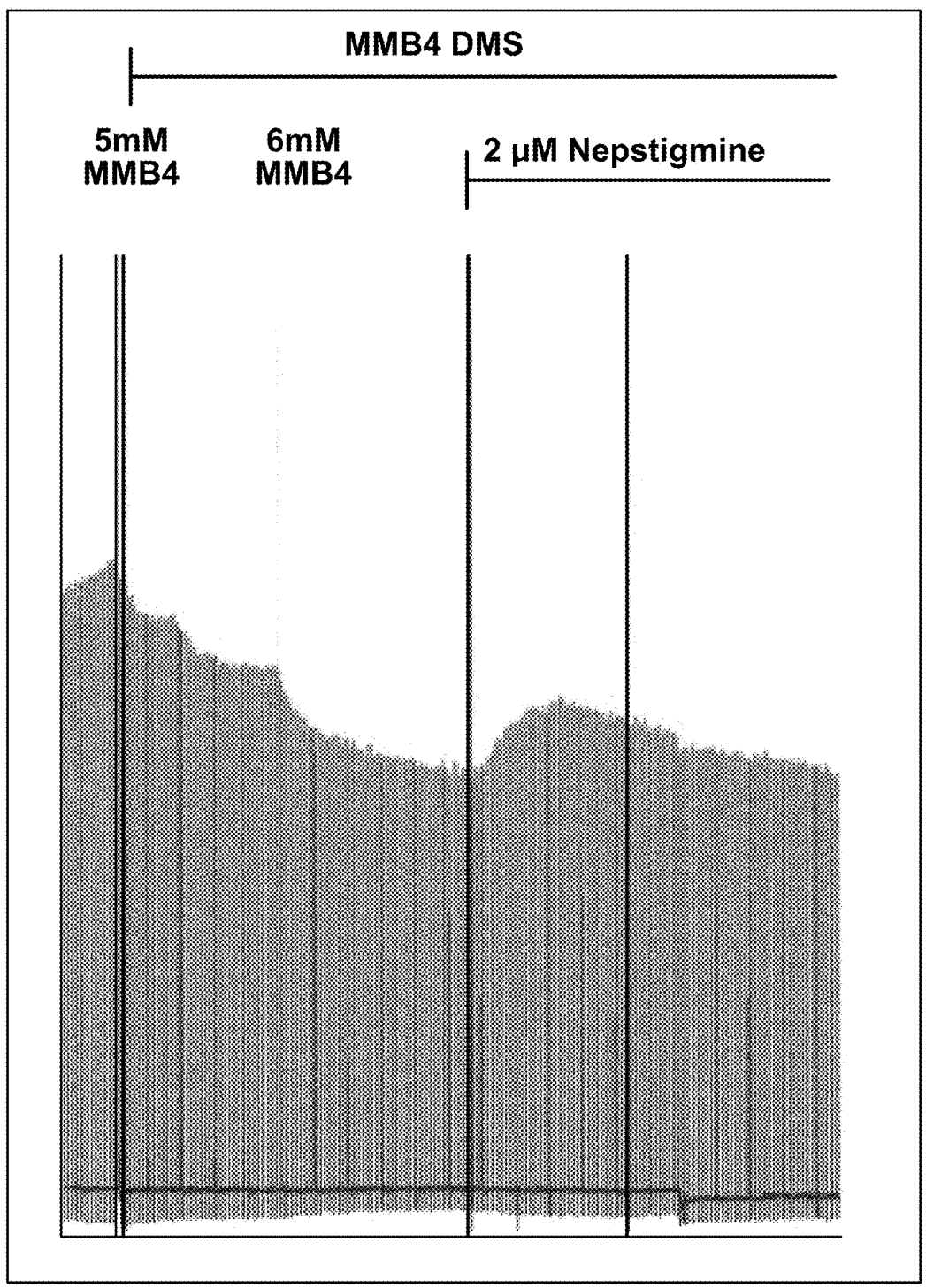
FIG. 20 depicts a representative trace of the stimulatory effect of 2 pM neostigmine after a 50% reduction in muscle contraction amplitude with MMB4 DMS in rat left phrenic nerve-diaphragm preparation.

To determine if the inhibitor effect of MMB4 DMS could be rescued, neostigmine (2 pM) was added when reduction in contraction achieved 50%. Shown in Table 12 and FIG. 19, neostigmine partially increased contraction (0.6 g±0.1 g) and maximal rate of change (20±4 g/s) (representative trace in FIG. 20).

TABLE 12

Effects of neostigmine when added after a 50% reduction with MMB4 DMS on contraction amplitude and its maximal rate of change in rat left phrenic nerve-diaphragm preparation; represented as raw values and as time controlled adjusted changes from baseline ± SEM (n = 4).

| | | Neostigmine | |
|---|---|---|---|
| Dose (μM) | Parameter | Raw Values | Δ from 50% reduction with MMB4 |
| Baseline | Contraction Amplitude (g) | 9.8 ± 0.7 | 4.1 ± 0.4 |
| | Max Rate of Change (g/s) | 256 ± 22 | 123 ± 17 |
| 50% reduction with MMB4 | Contraction Amplitude (g) | 5.7 ± 0.5 | — |
| | Max Rate of Change (g/s) | 133 ± 12 | — |
| 2 | Contraction Amplitude (g) | 6.3 ± 0.5 | 0.6 ± 0.1 |
| | Max Rate of Change (g/s) | 153 ± 12 | 20 4 |

Figure 21:
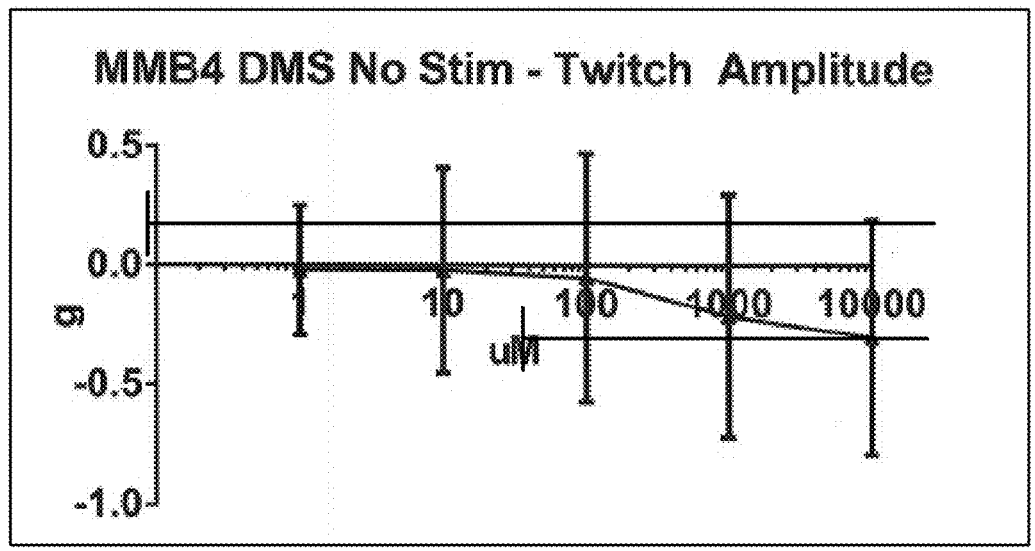
FIG. 21 depicts the effects of MMB4 DMS without nerve stimulation on muscle tension in rat left phrenic nerve-diaphragm preparation; represented as time controlled adjusted changes from baseline±SEM (n=5).
Figure 22:
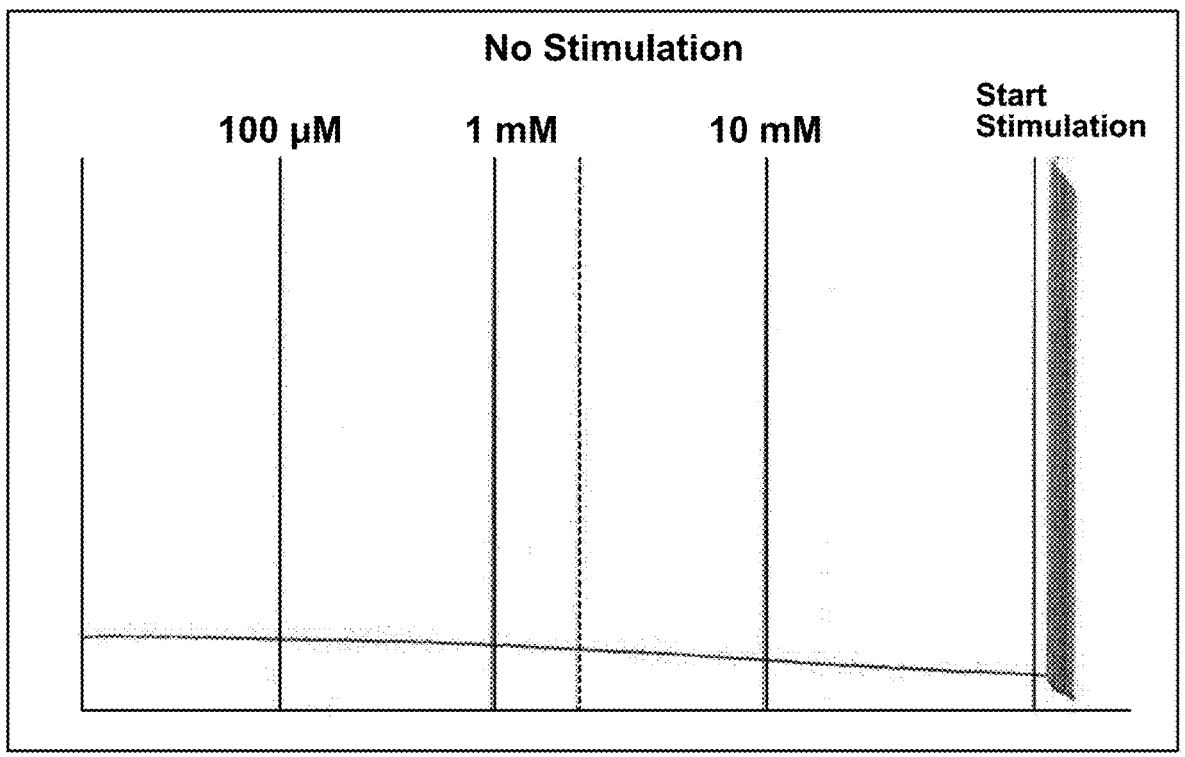
FIG. 22 depicts a representative trace of 100 pM, 1 mM, and 10 mM MMB4 DMS with 15 minutes in between doses in rat left phrenic nerve-diaphragm preparation without stimulation.

The effect of MMB4 DMS on muscle tension without stimulation was tested and had a minimal effect when compared to non-stimulated time controls (Table 13 and FIG. 21) (representative trace in FIG. 22).

TABLE 13

Effects of MMB4 DMS without nerve stimulation on muscle tension in rat left phrenic nerve-diaphragm preparation; represented as raw values and as time controlled adjusted changes from baseline ± SEM (n = 5).

| | | MMB4 DMS | |
|---|---|---|---|
| Dose (μM) | Parameter | Raw Values | Δ from BL |
| Baseline | Contraction Amplitude (g) | 4.3 ± 0.3 | — |
| | Max Rate of Change (g/s) | — | — |
| 1 | Contraction Amplitude (g) | 4.2 ± 0.4 | −0.02 ± 0.27 |
| | Max Rate of Change (g/s) | — | — |
| 10 | Contraction Amplitude (g) | 4.2 ± 0.5 | −0.02 ± 0.43 |
| | Max Rate of Change (g/s) | — | — |
| 100 | Contraction Amplitude (g) | 4.2 ± 0.6 | −0.05 ± 0.52 |
| | Max Rate of Change (g/s) | — | — |
| 1000 | Contraction Amplitude (g) | 4.1 ± 0.6 | −0.21 ± 0.51 |
| | Max Rate of Change (g/s) | — | — |
| 10000 | Contraction Amplitude (g) | 3.3 ± 0.8 | −0.3 ± 0.49 |
| | Max Rate of Change (g/s) | — | — |

Figure 23:
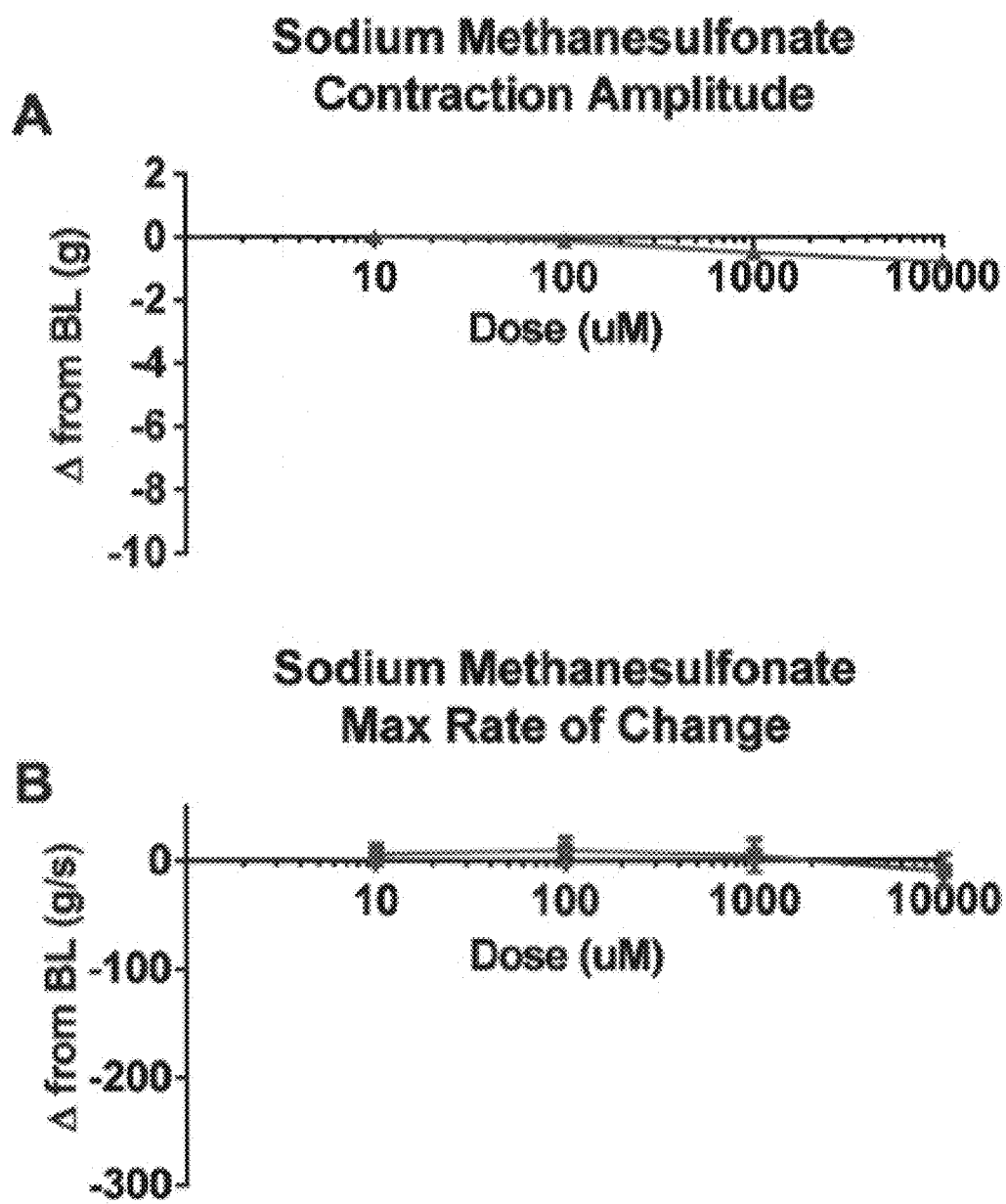
FIG. 23 depicts the effects of sodium methanesulfonate on (A) contraction amplitude and (B) maximal rate of change in rat left phrenic nerve diaphragm preparation; represented as time controlled adjusted changes from baseline±SEM (n=5).
Figure 24:
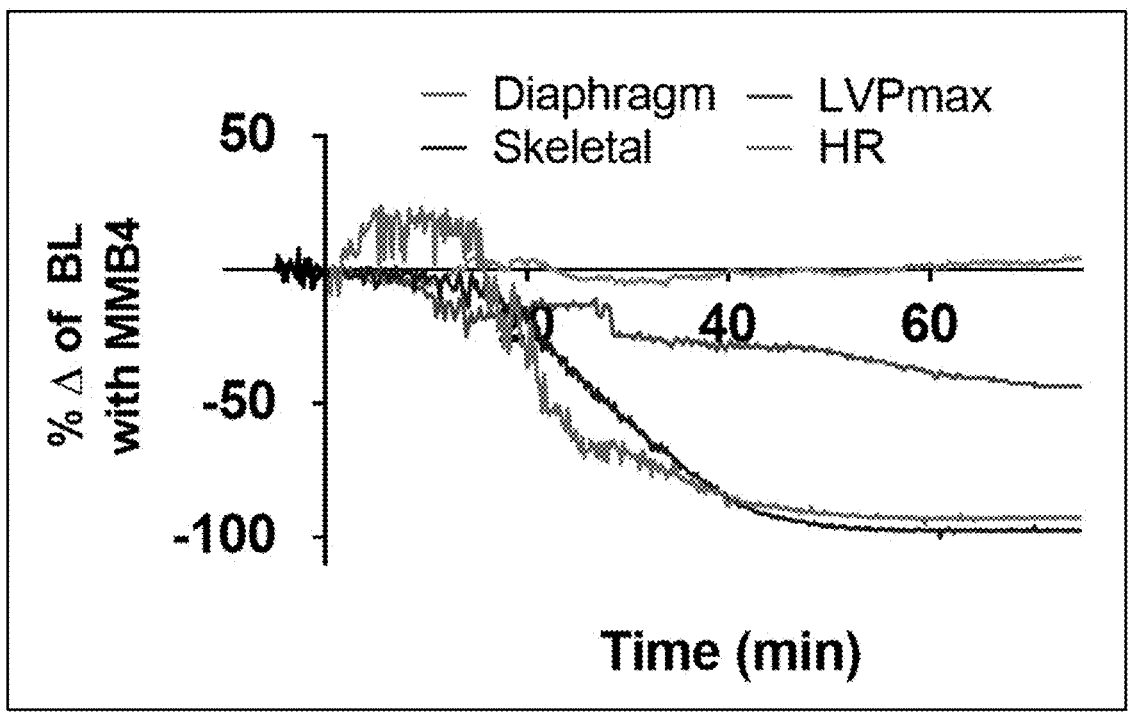
FIG. 24 depicts a graph showing the accumulative dose effects of IV administration of MMB4 at 8.33 mg/kg/min in ventilated anesthetized rabbits.
Figure 25:
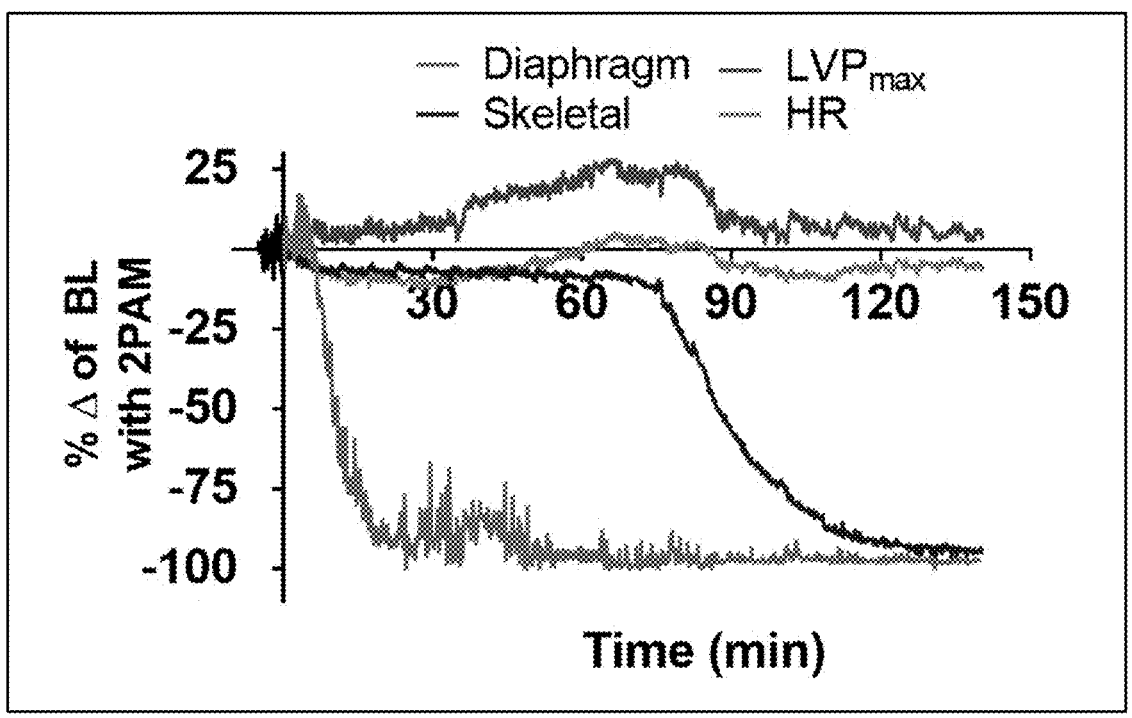
FIG. 25 depicts a graph showing the accumulative dose effects of IV administration of 2PAM at 2.5 mg/kg/min in ventilated anesthetized rabbits.

Sodium Methanesulfonate Assessment:

To determine if the vehicle counter ion of MMB4 DMS (sodium methanesulfonate, SMS), has any function effects, SMS was tested under similar concentrations as MMB4 DMS. Shown in Table 14 and FIG. 23, SMS had minimal effect on function.

TABLE 14

Effects of sodium methane sulfonate on contraction amplitude and its maximal rate of change in rat left phrenic nerve diaphragm preparation; represented as raw values and as time controlled adjusted changes from baseline ± SEM (n = 5).

| Dose (µM) | Parameter | Sodium Methanesulfonate Raw Values | Δ from BL |
|---|---|---|---|
| Baseline | Contraction Amplitude (g) | 9.0 ± 0.8 | — |
|  | Max Rate of Change (g/s) | 207 ± 46 | — |
| 10 | Contraction Amplitude (g) | 9.1 ± 0.8 | 0.0 ± 0.2 |
|  | Max Rate of Change (g/s) | 211 ± 48 | 6 ± 9 |
| 100 | Contraction Amplitude (g) | 8.9 ± 0.8 | −0.1 ± 0.2 |
|  | Max Rate of Change (g/s) | 214 ± 48 | 9 ± 12 |
| 1000 | Contraction Amplitude (g) | 8.6 ± 0.8 | −0.5 ± 0.2 |
|  | Max Rate of Change (g/s) | 210 ± 48 | 4 ± 15 |
| 10000 | Contraction Amplitude (g) | 8.2 ± 0.7 | −0.8 ± 0.2 |
|  | Max Rate of Change (g/s) | 197 ± 45 | −11 ± 15 |

In conclusion, the vertical, phrenic nerve-diaphragm preparation can successfully detect test articles that strengthen, weaken, or change minimally force of contraction. The stimulatory portion of the biphasic effect with MMB4 DMS is likely a direct inhibitory effect on AChE (similar to observation with a similar oxime, 2-PAM (Goyer, 1968). Since the addition on an AChE inhibitor (neostigmine) partially rescued MMB4 DMS when contraction amplitude was reduced by 50%, the blockage observed at higher doses is not the result of desensitization due to persistent depolarization and likely due to nicotinic antagonism, either at the receptor or receptor linked ion gate channel level. This effect is consistent with the effects of other oximes (Goyer, 1968; Alkondon et al., 1988; Tattersall, 1993). As SMS did not elicit a function effect, the functional effect of MMB4 is not due to the counter ion, DMS.

REFERENCES

Naguib M and Lien C A. "Pharmacology of Muscle Relaxants and Their Antagonists". Chapter 29, pp 859-911. Miller's Anesthesiology (edited by Ronald D. Miller; consulting editors L I Eriksson, L A Fleisher, J P Wiener-Kronish, W L Young), 7th edition, Published by Churchill, Livingstone, Elsevier; 2010.

Foldes, F F, McNall P G, Borrego-Hinojosa J M: Succinylcholine, a new approach to muscular relaxation in anaesthesiology. N Engl J Med 247:596-600, 1952.

All percentages and ratios are calculated by weight unless otherwise indicated.

All percentages and ratios are calculated based on the total composition unless otherwise indicated.

Every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and de-scribed, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inducing neuromuscular blockade via modulation of a nicotinic receptor in an individual in need thereof, comprising administering an oxime or pharmaceutically acceptable salt thereof, an analgesic, and an anesthetic to said individual, wherein said oxime or pharmaceutically acceptable salt thereof is administered in an amount that achieves cessation of a muscle contraction, wherein said muscle is skeletal muscle.

2. The method of claim 1, wherein said oxime is selective for diaphragm muscle.

3. The method of claim 1, wherein said oxime is selective for peripheral skeletal muscle.

4. The method of claim 1, wherein said oxime is selective for both diaphragm muscle and or peripheral skeletal muscle.

5. The method of claim 1, wherein said oxime is selected from one or more of

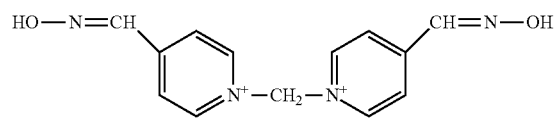 [SMILES: ON=Cc1cc[n+](C[n+]2ccc(C=NO)cc2)cc1]

(methoxime or "MMB4");

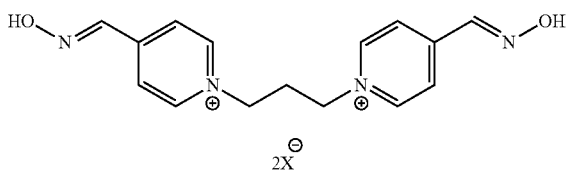 [SMILES: O/N=C/c1cc[n+](CCC[n+]2ccc(/C=N/O)cc2)cc1]

(trimedoxime or "TMB-4" or 1,3-bis(5-hydroxyiminomethylpyridinium)-propane bromide));

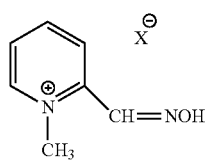

(pralidoxime or "2-PAM" or 2-hydroxyiminomethyl-1-methylpyridinium chloride);

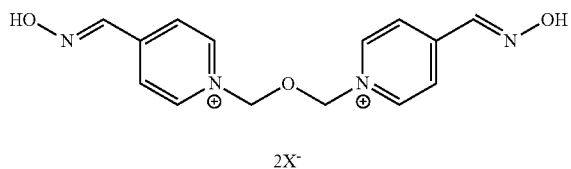 [SMILES: O/N=C/c1cc[n+](COC[n+]2ccc(/C=N/O)cc2)cc1]

(obidoxime or [1,3bis(4-hydroxyimino-methylpyridinium)-2-oxapropane);

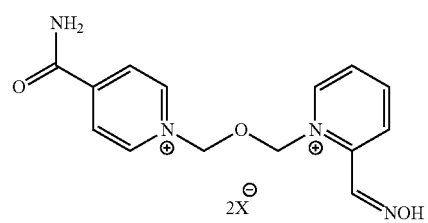

("HI-6" or [1-(2hydroxyiminomethylpyridinium)-3-(4-carbamoylpryidinium)-2-oxapropane chloride],

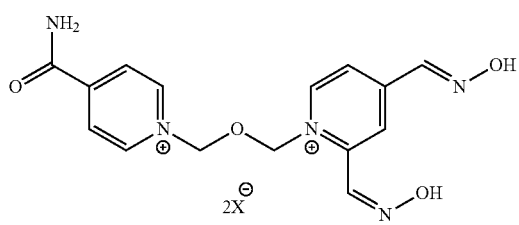 [SMILES: NC(=O)c1cc[n+](COC[n+]2ccc(/C=N/O)cc2/C=N\O)cc1]

HLo-7" or (1-[2,4-bis(hydroxyiminomethylpyridinium)]-3-(4-carbamoylpyridinium)-2-oxapropane chloride;

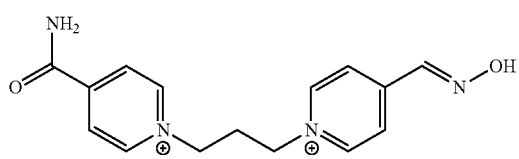 [SMILES: NC(=O)c1cc[n+](CCC[n+]2ccc(/C=N/O)cc2)cc1]

("K027" or [1-(4hydroxyiminomethylpyridinium)-3(4-carbamoylpyridinium)-propane bromide];
and pharmaceutically acceptable salts thereof.

6. The method of claim 1, wherein said oxime is MMB4 or a pharmaceutically acceptable salt thereof.

7. The method of claim 1, wherein said pharmaceutically acceptable salt thereof is selected from dichloride or dimethane sulfonate.

8. The method of claim 1, wherein said oxime is administered prior to or during a surgical procedure.

9. The method of claim 1, wherein said oxime is administered via a route selected from intravenously, parenterally, intramuscularly, or a combination thereof.

10. The method of claim 1, wherein said oxime administered as a composition comprising from about 25 to about 500 mg/mL, or from about 50 to about 250 mg/mL or about 100 mg/mL oxime in a pharmaceutically acceptable carrier.

11. A composition comprising an oxime or pharmaceutically acceptable salt thereof in an isotonic solution, and further comprising an amnestic agent, an analgesic agent, and anti-salivation agent.

12. The composition of claim 11, wherein said isotonic solution is a saline solution.

13. The composition of claim 11, wherein said isotonic solution is a sterile solution.

14. The composition of claim 11, wherein said oxime is selected from one or more of

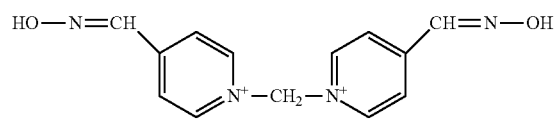 [SMILES: ON=Cc1cc[n+](C[n+]2ccc(C=NO)cc2)cc1]

(methoxime or "MMB4");

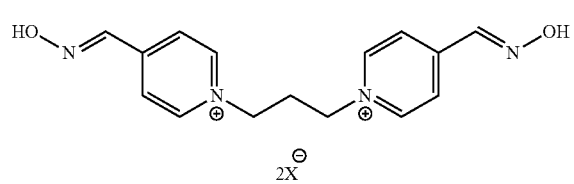 [SMILES: O/N=C/c1cc[n+](CCC[n+]2ccc(/C=N/O)cc2)cc1]

(trimedoxime or "TMB-4" or 1,3-bis(5-hydroxyiminomethylpyridinium)-propane bromide));

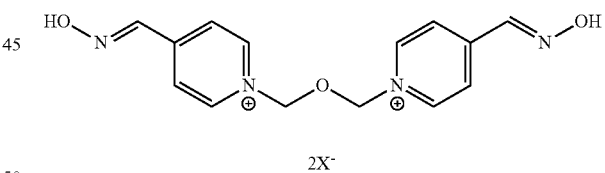

(obidoxime or [1,3bis(4-hydroxyimino-methylpyridinium)-2-oxapropane);

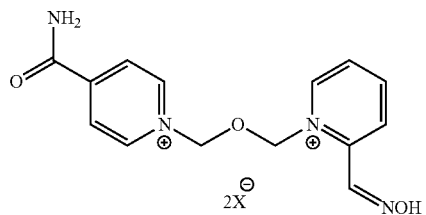

("HI-6" or [1-(2hydroxyiminomethylpyridinium)-3-(4-carbamoylpryidinium)-2-oxapropane chloride],

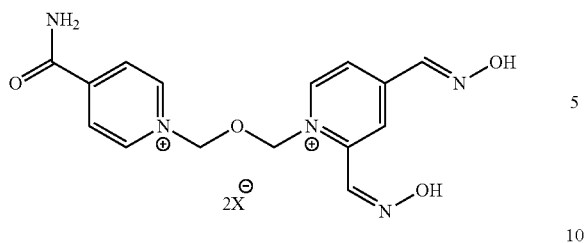

HLo-7" or (1-[2,4-bis(hydroxyiminomethylpyridinium)]-3-(4-carbamoylpyridinium)-2-oxapropane chloride;

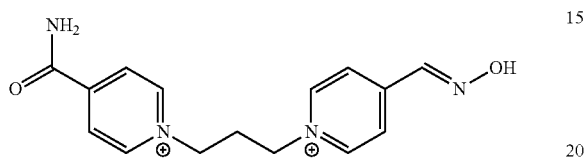

("K027" or [1-(4hydroxyiminomethylpyridinium)-3(4-carbamoylpyridinium)-propane bromide];
and pharmaceutically acceptable salts thereof.

15. The composition of claim 11, wherein the oxime or pharmaceutically acceptable salt thereof is present in concentration of about 25 to about 500 mg/mL in the isotonic solution.

16. The composition of claim 11 further comprising a neuromuscular blocker.

* * * * *